(12) United States Patent
Shinar et al.

(10) Patent No.: US 11,207,170 B2
(45) Date of Patent: *Dec. 28, 2021

(54) SYSTEMS, METHODS AND DEVICES FOR EMBOLIC PROTECTION

(71) Applicant: Javelin Medical Ltd., Rehovot (IL)

(72) Inventors: Guy Shinar, Ramat Gan (IL); Ofer Yodfat, Modi'in (IL)

(73) Assignee: JAVELIN MEDICAL LTD., Yokneam (IL)

( * ) Notice: Subject to any disclaimer, the term of this patent is extended or adjusted under 35 U.S.C. 154(b) by 146 days.

This patent is subject to a terminal disclaimer.

(21) Appl. No.: 16/270,310

(22) Filed: Feb. 7, 2019

(65) Prior Publication Data

US 2019/0343612 A1 Nov. 14, 2019

Related U.S. Application Data

(63) Continuation of application No. 14/947,678, filed on Nov. 20, 2015, now Pat. No. 10,226,321, which is a
(Continued)

(51) Int. Cl.
*A61F 2/01* (2006.01)
*A61B 17/04* (2006.01)
(Continued)

(52) U.S. Cl.
CPC ............ *A61F 2/01* (2013.01); *A61B 17/0401* (2013.01); *A61B 17/0487* (2013.01);
(Continued)

(58) Field of Classification Search
CPC ...... A61F 2/013; A61F 2/01; A61F 2002/016; A61F 2230/0067; A61F 2230/008; A61F 2230/0091; A61F 2002/015
See application file for complete search history.

(56) References Cited

U.S. PATENT DOCUMENTS

| 3,540,431 A | 11/1970 | Mobin-Uddin |
| 4,425,908 A | 1/1984 | Simon |
| (Continued) | | |

FOREIGN PATENT DOCUMENTS

| CN | 2601642 | 2/2004 |
| CN | 1911188 A | 2/2007 |
| (Continued) | | |

OTHER PUBLICATIONS

Supplementary European Search Report issued for EP 17862315, dated Mar. 25, 2020.
(Continued)

*Primary Examiner* — Katherine M Shi
(74) *Attorney, Agent, or Firm* — Cooley LLP

(57) ABSTRACT

Embodiments of the present disclosure are directed to systems, methods and devices for providing embolic protection in a patient. In some embodiments, the device is configured for implantation in a body vessel including fluid flow. The device may assume, or be constrained to assume, an undeployed state and a deployed state. In the undeployed state, the device or a portion thereof has a substantially linear shape configured to reside in the lumen of a thin needle having a diameter of less than about 0.5 mm (for example), in the deployed state, the device has a primary axis. When the device is implanted the primary axis is approximately perpendicular to the fluid flow. In some embodiments, the device comprises a thin filament body. In the deployed state the filament takes a helical shape. Emboli that are larger than the distance between consecutive turns or windings of the helix are thus filtered by the device and are prevented from causing deleterious conditions such as stroke or pulmonary embolism. The device may be made of a super-elastic alloy. Thus, the device may transition between the undeployed and the deployed states without plastic deformation. Delivery
(Continued)

systems and method for implanting such devices are also disclosed.

21 Claims, 28 Drawing Sheets

Related U.S. Application Data continuation of application No. 14/552,890, filed on Nov. 25, 2014, now Pat. No. 9,220,588, which is a continuation of application No. PCT/IB2013/001336, filed on May 30, 2013.

(60) Provisional application No. 61/653,676, filed on May 31, 2012, provisional application No. 61/693,979, filed on Aug. 28, 2012, provisional application No. 61/746,423, filed on Dec. 27, 2012, provisional application No. 61/754,264, filed on Jan. 18, 2013.

(51) Int. Cl.
*A61B 17/12* (2006.01)
*A61B 17/00* (2006.01)
*A61B 90/00* (2016.01)
*A61B 17/122* (2006.01)

(52) U.S. Cl.
CPC .. *A61B 17/12031* (2013.01); *A61B 17/12036* (2013.01); *A61B 17/12109* (2013.01); *A61B 17/12145* (2013.01); *A61B 17/0467* (2013.01); *A61B 17/122* (2013.01); *A61B 90/39* (2016.02); *A61B 2017/00004* (2013.01); *A61B 2017/045* (2013.01); *A61B 2017/0409* (2013.01); *A61B 2017/0417* (2013.01); *A61B 2017/0464* (2013.01); *A61B 2017/0496* (2013.01); *A61B 2017/12063* (2013.01); *A61F 2/011* (2020.05); *A61F 2002/016* (2013.01); *A61F 2230/0071* (2013.01); *A61F 2230/0091* (2013.01); *A61F 2250/0098* (2013.01)

(56) References Cited

U.S. PATENT DOCUMENTS

| | | |
|---|---|---|
| 4,494,531 A | 1/1985 | Gianturco |
| 4,722,350 A | 2/1988 | Armeniades et al. |
| 5,059,205 A | 10/1991 | El-Nounou et al. |
| 5,350,397 A | 9/1994 | Palermo et al. |
| 5,413,586 A | 5/1995 | Dibie et al. |
| 5,634,942 A | 6/1997 | Chevillon et al. |
| 5,649,949 A | 7/1997 | Wallace et al. |
| 5,733,329 A | 3/1998 | Wallace et al. |
| 5,800,454 A | 9/1998 | Jacobsen et al. |
| 5,868,754 A | 2/1999 | Levine et al. |
| 5,957,940 A | 9/1999 | Tanner et al. |
| 5,976,172 A | 11/1999 | Homsma et al. |
| 6,007,558 A | 12/1999 | Ravenscroft et al. |
| 6,059,825 A | 5/2000 | Hobbs et al. |
| 6,074,341 A | 6/2000 | Anderson et al. |
| 6,093,199 A | 7/2000 | Brown et al. |
| 6,099,549 A | 8/2000 | Bosma et al. |
| 6,123,715 A | 9/2000 | Amplatz |
| 6,152,144 A | 11/2000 | Lesh et al. |
| 6,214,025 B1 | 4/2001 | Thistle et al. |
| 6,238,403 B1 | 5/2001 | Greene, Jr. et al. |
| 6,344,052 B1 | 2/2002 | Greenan et al. |
| 6,368,346 B1 | 4/2002 | Jadhav et al. |
| 6,375,671 B1 | 4/2002 | Kobayashi et al. |
| 6,395,017 B1 | 5/2002 | Dwyer et al. |
| 6,652,558 B2 | 11/2003 | Patel et al. |
| 6,669,707 B1 | 12/2003 | Swanstrom et al. |
| 6,673,089 B1 | 1/2004 | Yassour et al. |
| 6,730,108 B2 | 5/2004 | Van Tassel et al. |
| 7,128,073 B1 | 10/2006 | Van der Burg et al. |
| 7,144,363 B2 | 12/2006 | Pai et al. |
| 7,261,731 B2 | 8/2007 | Patel et al. |
| 7,306,624 B2 | 12/2007 | Yodfat et al. |
| 7,572,273 B2 | 8/2009 | Mazzocchi et al. |
| 7,704,267 B2 | 4/2010 | Tessmer |
| 7,716,801 B2 | 5/2010 | Douk et al. |
| 7,740,644 B2 | 6/2010 | Beulke et al. |
| 7,794,494 B2 | 9/2010 | Sahatjian |
| 8,057,507 B2 | 11/2011 | Horan et al. |
| 8,118,858 B2 | 2/2012 | Tseng et al. |
| 8,137,396 B2 | 3/2012 | Busold et al. |
| 8,206,412 B2 | 6/2012 | Galdonik et al. |
| 8,221,446 B2 | 7/2012 | Pal et al. |
| 8,236,009 B2 | 8/2012 | Saadat et al. |
| 9,220,588 B2 | 12/2015 | Shinar et al. |
| 9,592,110 B1 | 3/2017 | Dan et al. |
| 10,028,819 B2 | 10/2018 | Shinar et al. |
| 10,226,321 B2 | 3/2019 | Shinar et al. |
| 10,507,023 B2 | 12/2019 | Poulsen |
| 10,531,943 B1 | 1/2020 | Dan et al. |
| 2001/0007946 A1 | 7/2001 | Lenker et al. |
| 2002/0010481 A1 | 1/2002 | Jayaraman |
| 2002/0188170 A1 | 12/2002 | Santamore et al. |
| 2003/0100939 A1 | 5/2003 | Yodfat et al. |
| 2004/0082962 A1 | 4/2004 | Demarais et al. |
| 2005/0004575 A1 | 1/2005 | Sgro et al. |
| 2005/0177181 A1 | 8/2005 | Kagan et al. |
| 2006/0167489 A1 | 7/2006 | Satake et al. |
| 2006/0212047 A1 | 9/2006 | Abbott et al. |
| 2007/0010857 A1 | 1/2007 | Sugimoto et al. |
| 2007/0066863 A1 | 3/2007 | Rafiee et al. |
| 2007/0156123 A1 | 7/2007 | Moll et al. |
| 2008/0108933 A1 | 5/2008 | Yu et al. |
| 2008/0183206 A1 | 7/2008 | Batiste |
| 2008/0221600 A1 | 9/2008 | Dieck et al. |
| 2008/0269789 A1 | 10/2008 | Eli |
| 2009/0054905 A1 | 2/2009 | Levy |
| 2009/0099591 A1 | 4/2009 | Nardone et al. |
| 2009/0138066 A1 | 5/2009 | Leopold et al. |
| 2009/0187211 A1 | 7/2009 | Mackiewicz |
| 2009/0228020 A1 | 9/2009 | Wallace et al. |
| 2010/0016881 A1 | 1/2010 | Fleck et al. |
| 2010/0234852 A1 | 9/2010 | Shinohara et al. |
| 2010/0268204 A1 | 10/2010 | Tieu et al. |
| 2010/0280522 A1 | 11/2010 | Barry et al. |
| 2011/0021984 A1 | 1/2011 | Kirschenman et al. |
| 2011/0022149 A1 | 1/2011 | Cox et al. |
| 2011/0137394 A1 | 6/2011 | Lunsford et al. |
| 2011/0226379 A2 | 9/2011 | Johnson |
| 2012/0165919 A1 | 6/2012 | Cox et al. |
| 2012/0172921 A1 | 7/2012 | Yamanaka et al. |
| 2012/0197379 A1 | 8/2012 | Laske et al. |
| 2012/0245614 A1 | 9/2012 | Drasler |
| 2012/0289988 A1 | 11/2012 | Riina et al. |
| 2012/0316597 A1 | 12/2012 | Fitz et al. |
| 2013/0184658 A1 | 7/2013 | Duncan |
| 2014/0004503 A1 | 1/2014 | Cima et al. |
| 2014/0114337 A1 | 4/2014 | Fung et al. |
| 2014/0135799 A1 | 5/2014 | Henderson |
| 2014/0277097 A1 | 9/2014 | Castleberry et al. |
| 2015/0148837 A1 | 5/2015 | Shinar et al. |
| 2015/0196301 A1 | 7/2015 | Bodewadt et al. |
| 2015/0297241 A1 | 10/2015 | Yodfat et al. |
| 2017/0367808 A1 | 12/2017 | Shinar et al. |
| 2018/0103960 A1 | 4/2018 | Poulsen |
| 2019/0021836 A1 | 1/2019 | Yair et al. |
| 2019/0167404 A1 | 6/2019 | Shinar et al. |
| 2019/0269413 A1 | 9/2019 | Yodfat et al. |

FOREIGN PATENT DOCUMENTS

| | | |
|---|---|---|
| CN | 2017/68049 U | 3/2011 |
| CN | 103313751 A | 9/2013 |
| DE | 10 2005 010222 A1 | 9/2006 |
| EP | 0121447 | 10/1984 |
| EP | 0865772 A1 | 9/1998 |
| WO | WO 91/04716 | 4/1991 |
| WO | WO 1998/034546 | 8/1998 |

(56) References Cited

FOREIGN PATENT DOCUMENTS

| WO | WO 2004/098420 | 11/2004 |
|---|---|---|
| WO | WO 2005/051235 | 6/2005 |
| WO | WO 2005/117750 A1 | 12/2005 |
| WO | WO 2006/055443 | 5/2006 |
| WO | WO 2006/084156 | 8/2006 |
| WO | WO 2008/042266 | 4/2008 |
| WO | WO 2008/127328 A1 | 10/2008 |
| WO | WO 2010/134914 A1 | 11/2010 |
| WO | WO 2011/014703 | 2/2011 |
| WO | WO 2012/094251 | 7/2012 |
| WO | WO 2013/179137 | 12/2013 |
| WO | WO 2014/102767 | 7/2014 |
| WO | WO 2014/111911 | 7/2014 |

OTHER PUBLICATIONS

Cogo et al. "Distribution of Thrombosis in Patients with Symptomatic Deep Vein Thrombosis" Arch Intern Med., 1993, vol. 153, p. 2777-2780.
Cousin et al. "Incidence et distribution des thromboses veineusesdes des membres inférieurs diagnostiquées par écho-doppler au décours de prothèses de hanche, de genou et de fractures de hanche. Résultats portant sur 5981 explorations et 2123 thromboses en dix ans" Journal des Maladies Vasculaires, 2011, vol. 36, No. 4, p. 243-253 (English summary).
Decousus et al. "A Clinical Trial of Vena Caval Filters in the Prevention of Pulmonary Embolism in Patients with Proximal Deep-Vein Thrombosis", The New England Journal of Medicine, 1998, vol. 338, No. 7, p. 409-415.
Ouriel et al. "The anatomy of deep venous thrombosis of the lower extremity", Journal of Vascular Surgery, 2000, vol. 31, p. 895-900.
Thors et al. "Resorbable Inferior Vena Cava Filters: Trial in an In-vivo Porcine Model" J Vasc Interv Radiol 2011, vol. 22, No. 3, Mar. 2011, 330-335.
International Search Report and Written Opinion for International Application No. PCT/IB2013/001336 dated Jan. 24, 2014,.
International Search Report for International Application No. PCT/IL13/50979 dated Jun. 23, 2014.
International Search Report for International Application No. PCT/IL13/50981 dated Jun. 23, 2014.
Supplementary European Search Report and European Search Opinion, dated Jan. 12, 2016, for European Application No. 13797107.3.
Supplementary European Search Report for European Application No. 13871655.0 dated Oct. 13, 2016.
International Search Report for International Application No. PCT/IL2016/050016 dated Jun. 9, 2016.
International Search Report for International Application No. PCT/IL2017/051157 dated May 7, 2018.

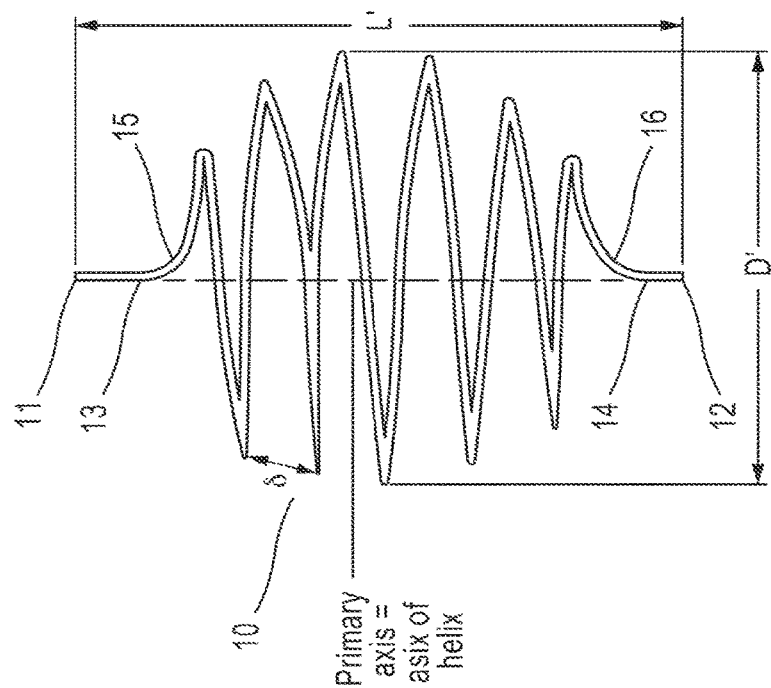
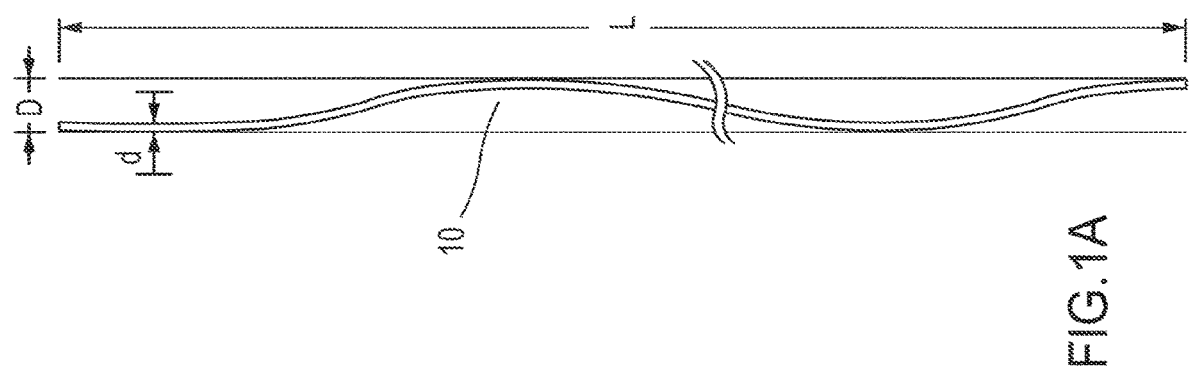
FIG. 1B
FIG. 1A

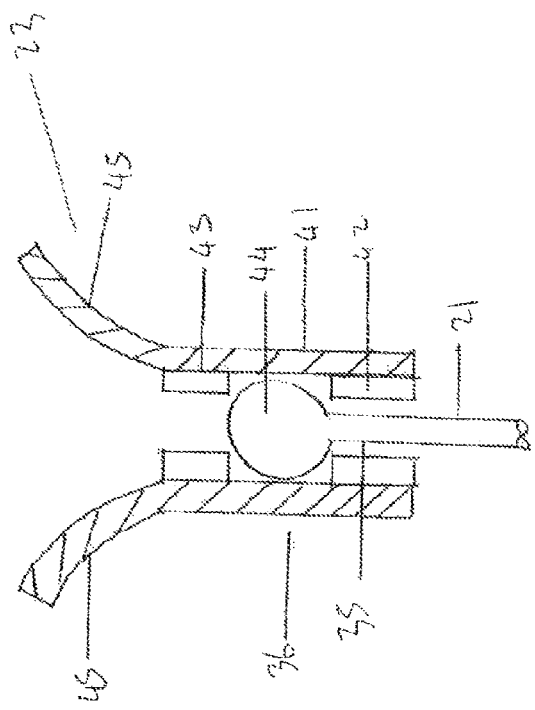
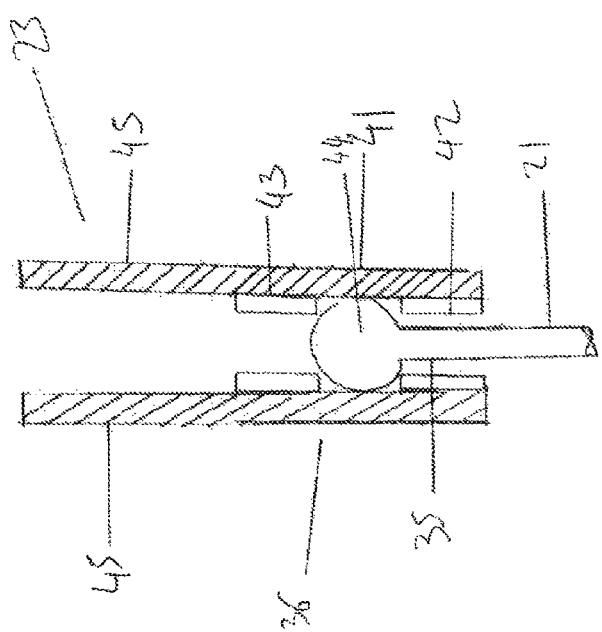
FIG. 4A
FIG. 4B

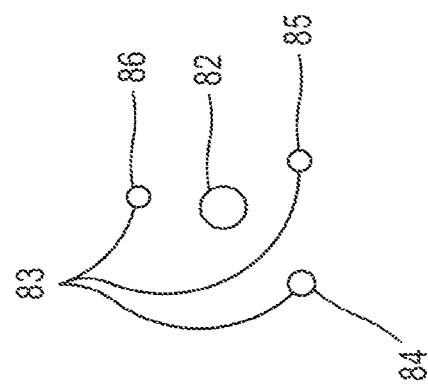
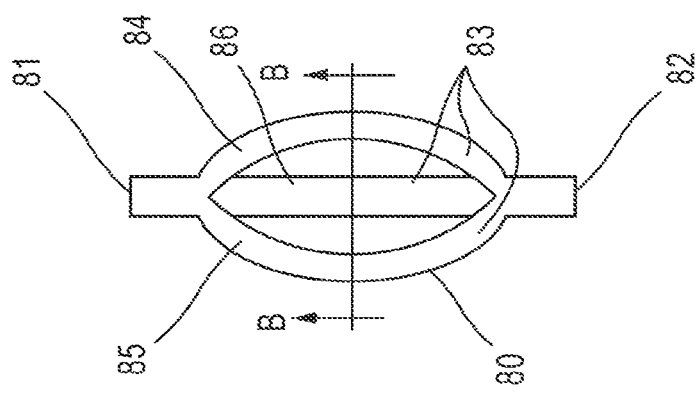
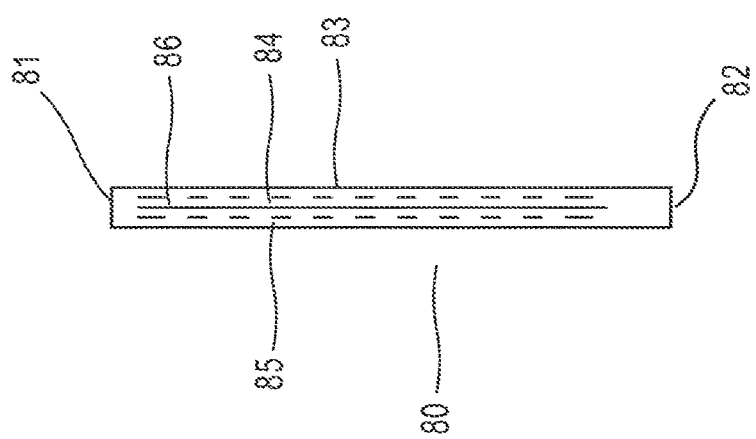

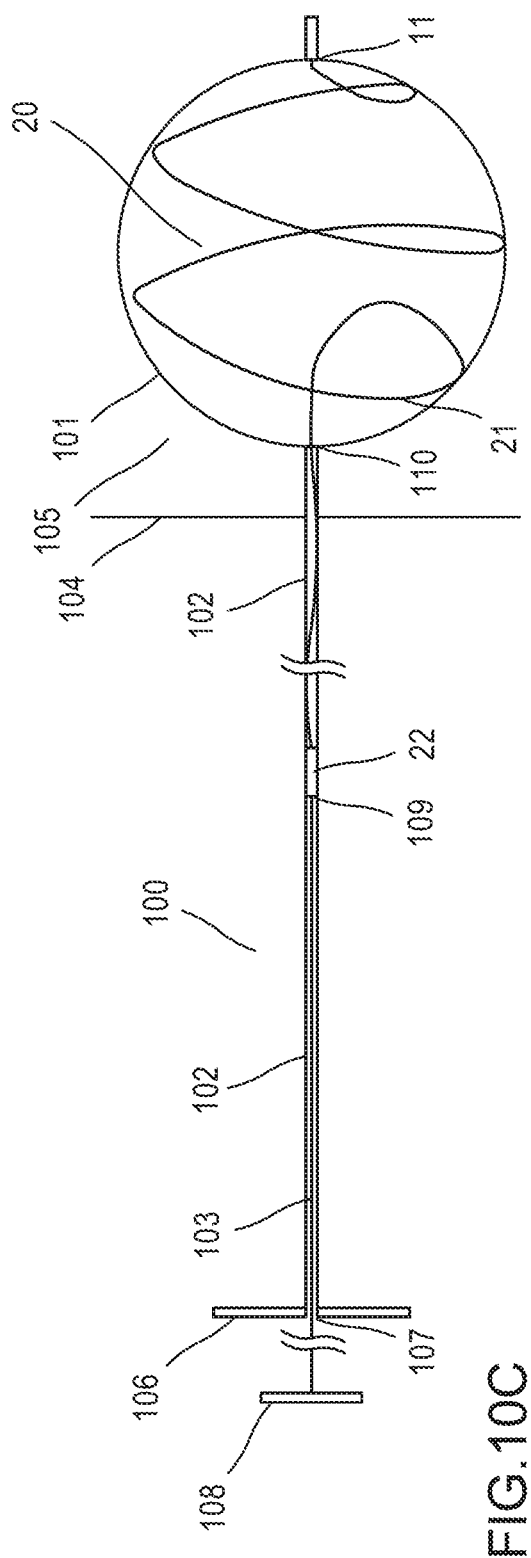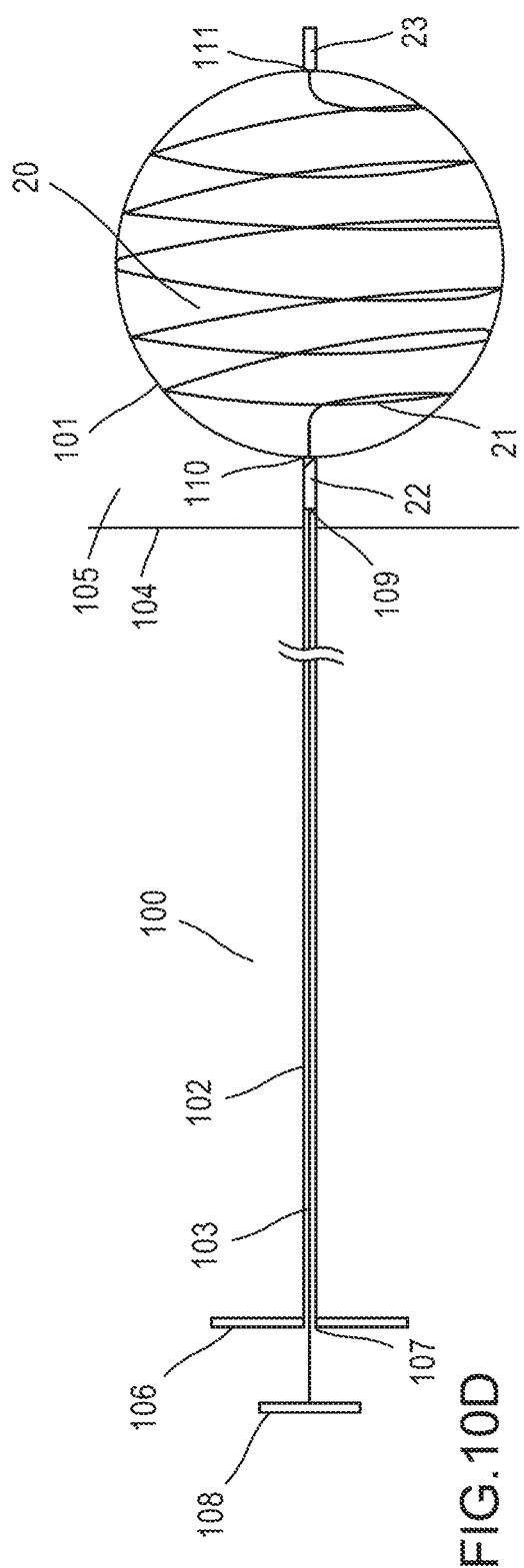

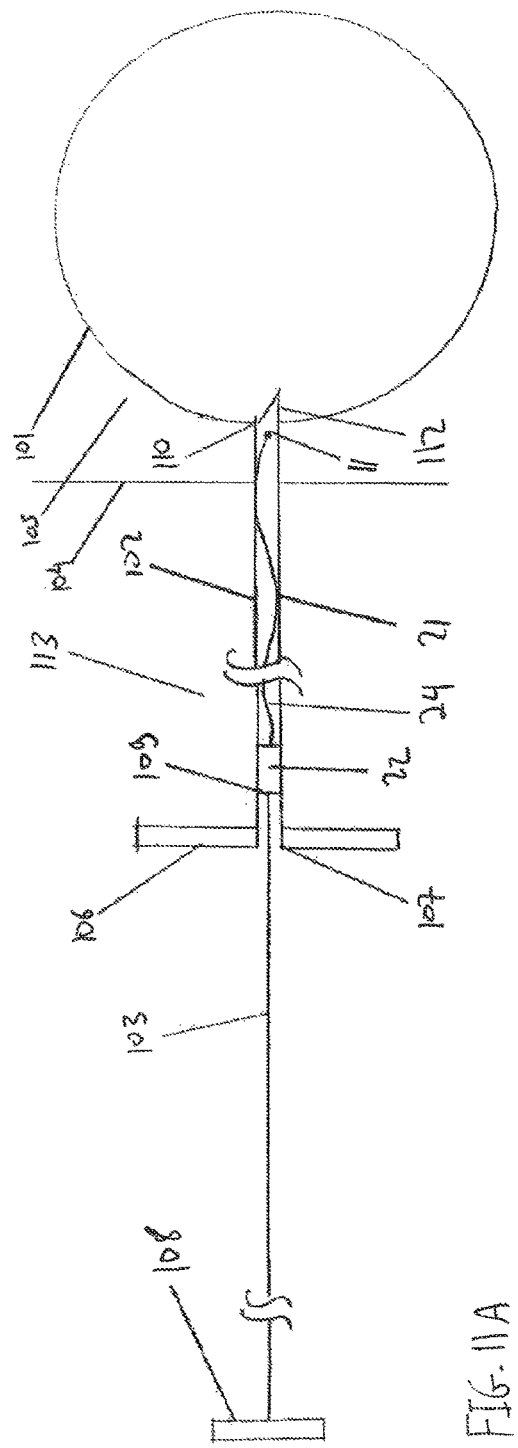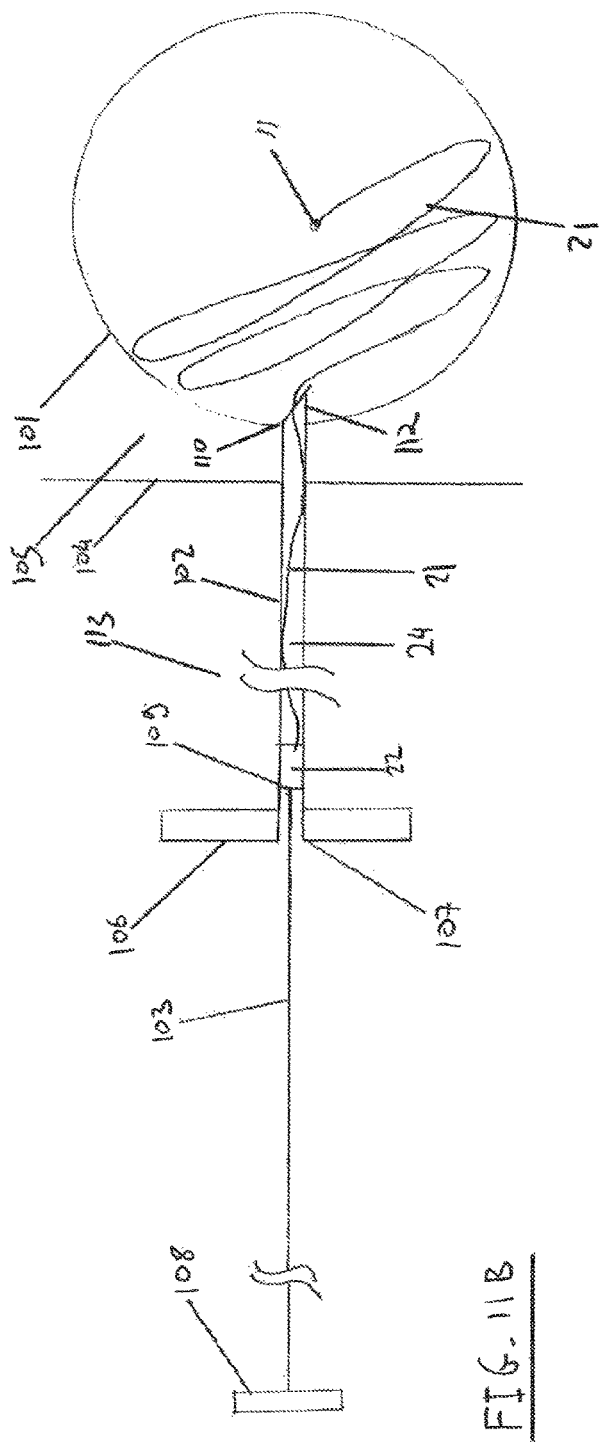
FIG. 11A
FIG. 11B

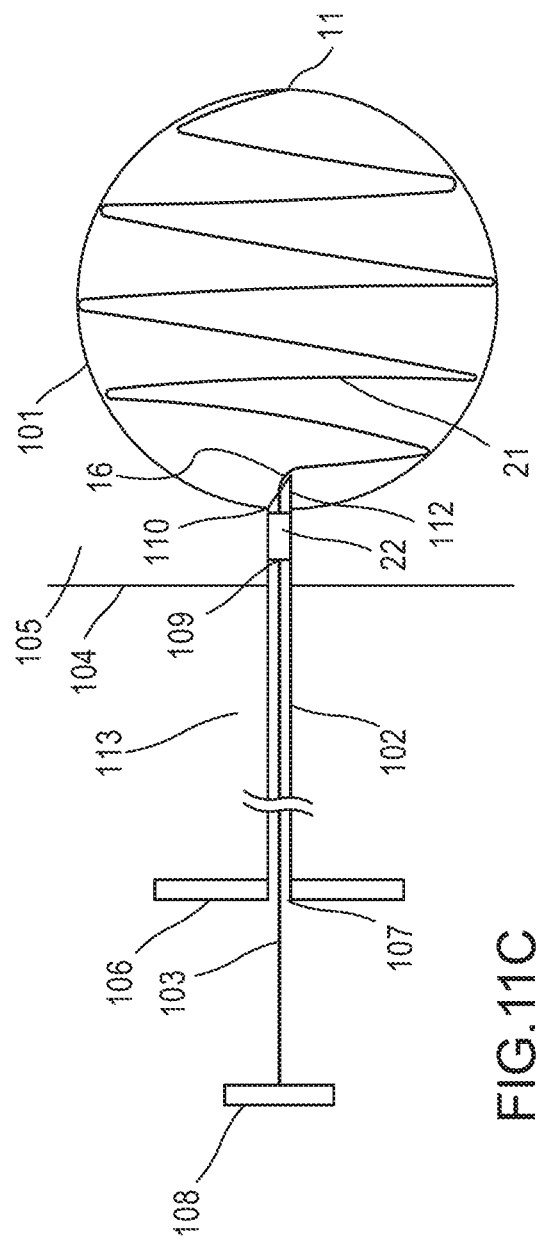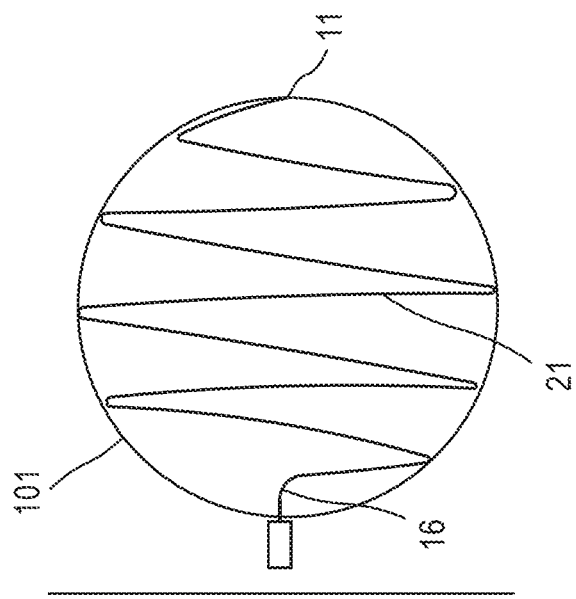

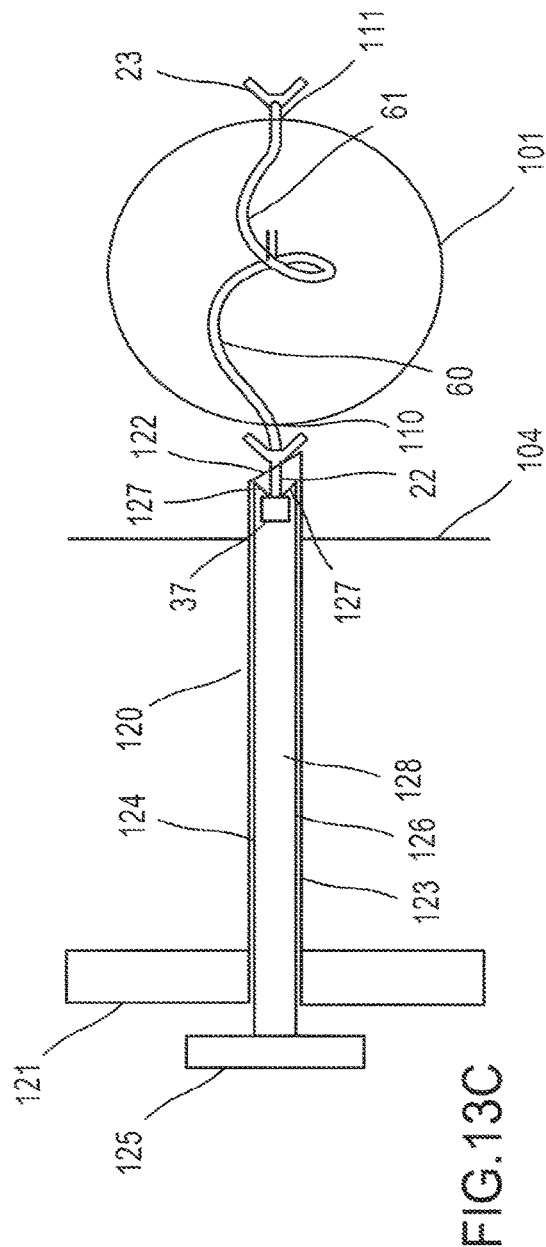
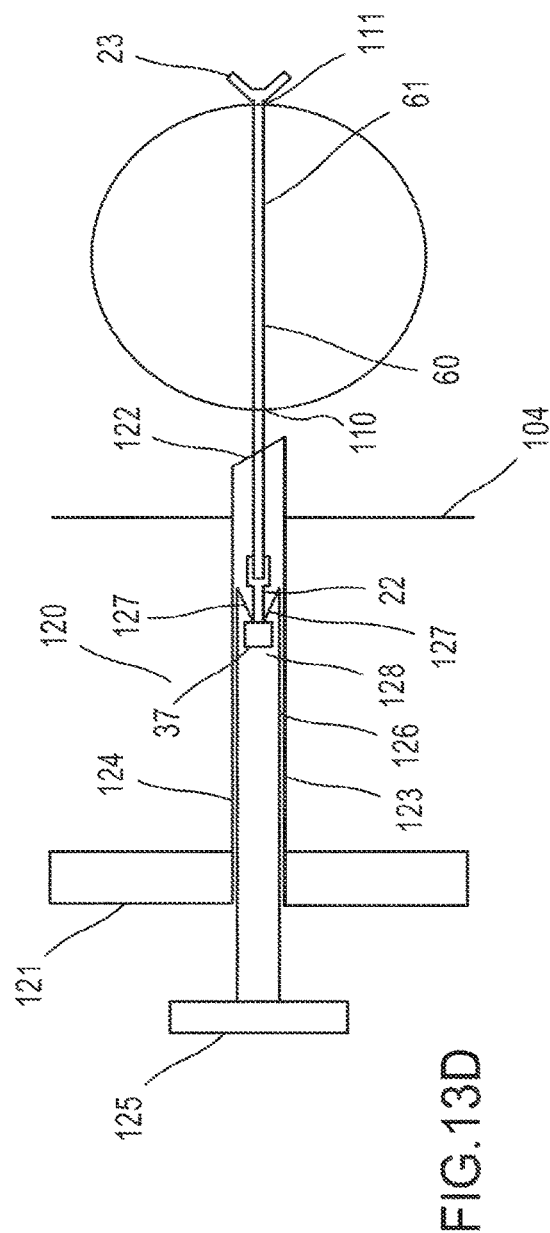
FIG.13C
FIG.13D

SYSTEMS, METHODS AND DEVICES FOR EMBOLIC PROTECTION

CROSS REFERENCE TO RELATED APPLICATIONS

This application is a continuation of and claims priority to U.S. application Ser. No. 14/947,678, filed Nov. 20, 2015, entitled "Systems, Methods and Devices for Embolic Protection", which is a continuation of U.S. application Ser. No. 14/552,890, filed Nov. 25, 2014, and entitled "Systems, Methods and Devices for Embolic Protection" (now U.S. Pat. No. 9,220,588, issued Dec. 29, 2015), which is a continuation of and claims priority to International Patent Application No. PCT/IB2013/001336, filed May 30, 2013, and entitled "Systems, Methods and Devices for Embolic Protection," which claims priority to and benefit of U.S. Provisional Patent Application No. 61/653,676, filed May 31, 2012, entitled "Apparatus and Methods of Providing Embolic Protection in a Patient," U.S. Provisional Patent Application No. 61/693,979, filed Aug. 28, 2012, entitled "Apparatus and Method of Providing Embolic Protection in a Body Vessel of a Patient," U.S. Provisional Patent Application No. 61/746,423, filed Dec. 27, 2012, entitled "Apparatus and Method of Monofilament Implant Delivery in a Body Vessel of a Patient," and U.S. Provisional Patent Application No. 61/754,264, filed Jan. 18, 2013, entitled "Monofilament Implants and Systems for Delivery Thereof." The present application incorporates herein by reference the disclosures of each of the above-referenced applications in their entireties.

FIELD OF THE DISCLOSURE

The field of the present disclosure is embolic protection devices. More specifically, the field of the present disclosure is embolic protection for the prevention of brain stoke and/or pulmonary embolism.

BACKGROUND OF THE DISCLOSURE

Embolism is the event of lodging of an embolus (a detached intravascular mass) into a narrow vessel, which causes a blockage in a distant part of the body. Embolism can be classified as to whether it enters the circulation in arteries or veins. Arterial embolism can start in the heart or in large arteries, and can cause occlusion and/or infarction in any part of the body. Embolus lodging in the brain from either the heart or the carotid arteries can cause an ischemic stroke. Venous embolism, which forms in systemic veins, can lodge in the lungs after passing through the right side of the heart. This deleterious condition is known as pulmonary embolism.

Distal embolization can occur spontaneously or be induced by manipulation of the heart, large arteries, or veins, either in the setting of open surgery, or in the setting of endovascular manipulation such as balloon angioplasty or stenting.

Distal embolization can be prevented by pharmacological treatment (anti-coagulants). While effective, anticoagulants have the deleterious side effect of high bleeding risk, which may be severe or even life-threatening. In addition, many patients do not tolerate well anticoagulant medication and cannot enjoy the embolic protection that it may render.

Distal embolization may also be prevented or by using mechanical filtering devices (distal embolic protection devices), which are placed between the embolic source and the distal vasculature. However, prior and current devices fail to adequately address the problem, and in fact, in many circumstances, cause problems (e.g., become occluded, migrate from the implantation site, and the like).

SUMMARY OF THE DISCLOSURE

In some embodiments, an embolic protection device (filtering device) is provided which includes a proximal end and a distal end, as well as an undeployed state and a deployed state.

In some embodiments, an embolic protection device is provided and comprises a wire or a filament, which may be made of a super-elastic alloy (e.g., nitinol). The device, which has a proximal and a distal end, may assume two states—a constrained, undeployed, substantially linear state and an expanded, deployed state, which may have a helical/helix shape. The device may be implanted within a blood vessel using a delivery system comprising a rigid needle (which in some embodiments may be referred to also as a "tube", both terms being used interchangeably, at least with respect to some embodiments, throughout) having an outer diameter of less than about 0.5 mm (about 1.5 French, 0.02") and a sharp distal end. The device may be preassembled within the needle and positioned at the distal end, where it may be constrained to assume its undeployed, substantially linear state. A pusher, in a form of an elongated rod, may also be preassembled within the needle, extending from the proximal end of the needle to the proximal end of the device. The implantation of the device is performed by piercing the skin and underlying tissues and advancing the needle into a vessel under ultrasound guidance. Within the vessel the device is exteriorized from the needle by pushing the pusher. After exteriorization of the device from the needle, the device assumes the expanded deployed helical state such that the distal end resides within the vessel lumen and the proximal end resides outside the vessel lumen. The axis of the helix ends up approximately perpendicular to the fluid flow within the vessel, and the windings or turns of the helix therefore exclude emboli whose size is larger than the distance between consecutive helix turns.

In some embodiments, the axis of the helix (and/or the device in general) may end tip at a predetermined angle relative to the fluid flow within the vessel, which may be between approximately 20 degrees and about 150 degrees, and in some embodiments, between about 30 degrees and 120 degrees, in some embodiments, between about 45 degrees and 100 degrees, and in some embodiments, between about 30 degrees and about 90 degrees.

The term "substantially," according to some embodiments, may be defined as near or proximate or about equal to, for example, a total amount, boundary or structure (and the like). In some embodiments, the term "substantially" may be defined as "essentially" (for example).

In some embodiments, a vascular embolic protection device for deployment at an implantation site within a blood vessel is provided and may include a filament having a length, proximal and distal ends and a diameter between about 0.025 mm and about 1 mm (and in some embodiments, between about 50 and 500 microns, for example), and is configured to include an undeployed state and a deployed state. In the undeployed state, at least a portion of the device is configured to fit within the lumen of a delivery tube, and in the deployed state, the device includes a primary axis which is approximately perpendicular to the fluid flow.

In some embodiments, the primary axis of device may be positioned at a predetermined angle relative to the fluid flow within the vessel, which may be between approximately 20 degrees and about 150 degrees, and in some embodiments, between about 30 degrees and 120 degrees, in some embodiments, between about 45 degrees and 100 degrees, and in some embodiments, between about 30 degrees and about 90 degrees.

Some of the embodiments may include one or more of the following features:

- a filament that has a length between about 7 mm and about 300 mm;
- at least one of the tube end and the distal end of the device is configured for puncturing the blood vessel in the vicinity of the implantation site;
- the length of a line segment connecting the proximal and the distal ends in the deployed state is greater than or about equal to the diameter of the blood vessel;
- the filament includes a substantially circular cross-section;
- the diameter of the filament is less than about 0.2 mm;
- the device includes a first proximal segment near the proximal end and a first distal segment near the distal end, and in the deployed state, the segments are substantially collinear with the primary axis;
- in the deployed state, the filament further comprises a proximal turn and a distal turn, and each turn resides in respective plane, and at least one of the planes approximately includes the primary axis;
- the filament further comprises a proximal segment near the proximal end, and in the deployed state the proximal segment is substantially collinear with said primary axis;
- in the deployed state, the filament further comprises a proximal turn residing in a plane that approximately includes the primary axis;
- at substantially every point along its length the radius of curvature exceeds a critical value equal to the diameter of the filament divided by about twice the critical strain of the material from which the filament is made. In some embodiments, the critical value is greater than about 0.6 mm;
- at least a portion of the filament in the undeployed state is configured in the shape of a helix whose pitch is much larger than its diameter;
- in the deployed state the filament has the shape of a helix comprising a plurality of turns, and depending upon the embodiment; the plurality of turns vary in diameter, the number of turns is between one and twenty, and/or a plurality of windings approximately trace the shape of a spherical shell having a diameter. In the case of the spherical shell, in some embodiments, the diameter of the spherical shell is less than or equal to the diameter of the vessel;
- in the deployed state the filament has the shape of a helix comprising a plurality of turns, and depending upon the embodiment: the distance between consecutive windings is greater than about 0.7 mm, or the distance between consecutive windings is less than about 1.5 mm;
- in the deployed state the filament has the shape of a helix comprising a plurality of turns, and depending upon the embodiment: the helix is compressed and exerts on the vessel wall a force approximately collinear with the helix axis, or the helix is not compressed;
- the filament comprises a hollow lumen;
- one or more of a radiopaque marker, an echogenic marker, a radioactive marker, a magnetic marker, and a magnetic resonance marker;
- the filament may be made from at least one of: a metal, a plastic, a natural polymer, a shape memory alloy, a super elastic alloy, a biodegradable material, a bioresorbable material, and a bioabsorbable material;
- an end piece arranged on at least one of the proximal end and the distal end, where, depending upon the embodiment:
  - each of the end pieces comprises at least one of a radiopaque marker, an echogenic marker, a radioactive marker, a magnetic marker, a magnetic resonance marker, an anchor, a non-traumatic tip, a bearing, and a retrieval knob,
  - each of the end pieces may be configured with an undeployed and a deployed state;
  - at least one of the end pieces may comprise an anchor, where the anchor may comprise at least one of a loop, a roughened surface, a barb, a micro-barb, a hook, a bulge, and a material configured to enlarge upon contact with an aqueous environment;
  - at least one of the end pieces may each separately be integral with the filament;
  - the radiopaque marker may comprise gold, platinum, a combination thereof and/or any other heavy metal (or combination thereof);
  - the echogenic marker may comprise one or more of a micro-bubble, micro bubble coating, and a cornerstone reflector;
  - the bearing may comprise housing and an axle, which may be configured to rotate in said housing with any degree of friction, and may be integral with the filament;
  - the hearing may be configured to release accumulated torsion or to prevent the build-up of torsion in the filament;
- the filament may be substantially straight in the deployed state (and in some embodiments, in the undeployed state);
- the shape of the filament may be substantially similar in both the undeployed and the deployed states;
- the device may further comprise two or more filaments, where each filament has a length, a diameter, a proximal filament end, and a distal filament end, as such, depending upon the embodiment, the filaments may joined at the proximal end and at the distal end of the device, and the two or more filaments each have a helical shape.

In some embodiments, a delivery device for delivering one and/or another device embodiments (for example) is provided, and may comprise a needle having a lumen, a sharp distal end and, an outer diameter less than about 1 mm, and a pusher slidable within the needle. The delivery device may also include at least one of a needle handle and a pusher handle.

In some embodiments, a method for implanting an embolic protection device in a patient's vessel containing fluid flow is provided and may include one or more, and in some embodiments, several, and, in some embodiments, all of the following steps: providing a needle having a lumen and a sharp distal end, providing a pusher slidable within the lumen of the needle, providing a device having a distal end, an undeployed state, and a deployed state having a primary axis, where at least a portion of the device is loaded within the lumen, making a puncture in a wall of the vessel using the sharp distal end of the needle or the distal end of the device, and exteriorizing the device through said needle and said puncture by advancing the pusher, retracting the needle, or both, such that said primary axis ends up approximately perpendicular to the fluid flow direction.

In some of such method embodiments, the method may further include the step of retracting the needle and the pusher from the patient, and/or making a second puncture at a location approximately diametrically opposed said puncture.

The device in such embodiments may be anchored proximate the puncture following exteriorization, and/or may be anchored at locations proximate the puncture and the second puncture following exteriorization.

Some method embodiments may further include the step of retrieving the embolic protection device from the patient's vessel.

Accordingly, some of the embodiments disclosed herein are configured to provide embolic, protection against stroke or pulmonary embolism, in any of an artery, a vein, an aorta, a common carotid artery, an internal carotid artery, a subclavian artery, a brachiocephalic artery, a renal artery, a vertebral artery, a superficial femoral vein, a deep femoral vein, a popliteal vein, an iliac vein, an inferior vena cava, and a superior vena cava. Such embolic protection may be permanent, or temporary, depending upon the embodiment.

In some embodiments, a retrieval apparatus for retrieving an implanted embolic protection device is provided and may comprise an extraction sheath having a lumen and a sharp end configured to pierce skin and to internalize said embolic protection device, and a grasper configured to irreversibly attach to said proximal end of the embolic protection device and to fit inside said lumen of said extraction sheath. The filtering device may be extracted from a patient through said extraction sheath.

In some embodiments, a device for occluding and/or ligating a patient's vessel is provided and may comprise an undeployed state and a deployed state, a filament comprising a proximal segment, a distal segment, and a separation point disposed between said proximal and distal segments, a distal anchor disposed at a distal end of said distal segment, and a slidable proximal anchor. The proximal anchor may be located in an undeployed state proximally to the separation point and in the deployed state distally to the separation point, and the proximal filament segment may be disconnected from the distal filament segment by applying mechanical and/or electrical energy to the separation point.

In some embodiments, a system for occluding and/or ligating a patient's vessel is provided and may comprise a device for occluding and/or ligating a patient's vessel (according to any one or another of such disclosed embodiments), a push tube configured to slidably receive the proximal segment of the filament and to push the slidable proximal anchor over the filament towards the distal anchor, and a delivery catheter comprising a hollow needle of less than about 1 mm in diameter, configured to slidably receive the push tube.

In some embodiments, a method for vessel ligation is provided and may comprise providing a system for occluding and/or ligating a patient's vessel (according to any such disclosed embodiments), puncturing a vessel wall at two diametrically-opposed sites, retracting the needle away from the device distal end allowing the distal anchor to engage tissue in its vicinity, and optionally further retracting the needle wherein the implant is exteriorized within the lumen of said vessel. In some embodiments, upon the needle end being retracted to a point external to the vessel lumen, the proximal anchor engages tissue in its vicinity. Further, in some embodiments, the method includes sliding the proximal anchor towards the distal anchor, resulting in external compression of the vessel and partial or complete adhering of the two opposing vessel walls. In some embodiments, one or more of the following steps may be performed: applying mechanical and/or electrical energy to the separation point, thereby separating the proximal filament segment from the rest of the device, and, exteriorizing the proximal filament segment from the patient.

In some embodiments, a method for embolic protection is provided and may include one or more of the following steps (in some embodiments, a plurality of these steps, and further still. In some embodiments, all of the following steps): providing a filtering device having an undeployed state and a deployed state having a primary axis, providing a delivery device comprising a needle having a lumen, said device configured to puncture tissue, making a puncture in a wall of a vessel using said delivery device, exteriorizing the filtering device through said puncture such that said primary axis ends up approximately perpendicular to the fluid flow within said vessel.

In some embodiments, an embolic protection device is provided for use in a patient's vessel, where the device may comprise proximal and distal ends, an undeployed state, and a deployed state having a primary axis. The device may be configured to pass through a needle while transitioning from the undeployed state to the deployed state, and in the deployed state, the primary axis may be approximately perpendicular to the fluid flow in the patient's vessel.

In some embodiments, an embolic protection device for use in a patient's vessel is provided, where the vessel includes a fluid flow and a lumen. The device may include proximal and distal ends, an undeployed state, and a deployed state having a primary axis. In the deployed state, the primary axis may be approximately perpendicular to the fluid flow and at least one of the proximal and distal ends resides exteriorly to the lumen.

In some embodiments, an embolic protection device for use in a patient's vessel is provided, and may comprise a filament having proximal and distal ends, an undeployed state, and a deployed state approximately shaped as a helix. In the deployed state the axis of the helix is roughly perpendicular to the fluid flow.

In some embodiments, an embolic protection device for use in a patient's vessel is provided. The device may comprise proximal and distal ends, an undeployed state, and a deployed state having a primary axis. In the deployed state the primary axis is approximately perpendicular to the longitudinal axis of the patient's vessel.

In some embodiments, a method for providing embolic protection in a patient is provided, where the method may include implanting a filament having a helical shape in a vessel of the patient, where vessel includes a fluid flow, such that the axis of the helix is approximately perpendicular to the fluid flow direction.

In some embodiments, in an undeployed state, the device, or a portion thereof, may assume or be constrained to assume, a substantially linear state. In the deployed state, the device may assume any shape resembling, or tracing the shell of, a body of revolution. In some embodiments, the axis of this body of revolution may be referred to as the "primary axis." For example, the device may assume, in the deployed state, a helical shape, where the primary axis is the axis of the helix. The device may be deployed in a body vessel having a fluid flow such that the primary axis is approximately perpendicular to the direction of the fluid flow.

In embodiments where the filament may possess a helical shape in the deployed state, the helical shape may comprise a plurality of windings or turns. The primary axis of the deployed state may roughly coincide with the axis of the helical shape. In some embodiments, the plurality of windings may roughly trace the shape of a spherical shell having a diameter. This diameter may be slightly less than the diameter of the target vessel.

In some embodiments, the deployed state of the device may be configured to trap emboli that might be present in the fluid flow. If, for example, the vessel is a carotid artery supplying blood to the brain, then the device may be configured to trap emboli originating, for example, in the heart and aorta and prevent them from causing brain stroke. If for example, the vessel is a femoral vein ultimately supplying blood to the lungs, then the device may be configured to trap emboli that originate, for example, in calf veins and may cause pulmonary embolism.

In some embodiments, in an undeployed, substantially linear state, the device may be configured to fit in the lumen of a thin tube or needle. The outer diameter of the tube or the needle may be less than about 1 mm, or even less than about 0.5 mm (for example). The puncture or punctures made by the needle in body tissue may be configured to be relatively small such that the risk of bleeding is minimal. The punctures, in some embodiments, may self-seal and self-heal.

In some embodiments, embolic protection devices of the present disclosure may comprise a single filament. The length of the filament, in some embodiments, may be in the range of about 7 mm to about 300 mm. The diameter of the filament, in some embodiments, may be less than about 0.2 mm.

In some embodiments, the distance between consecutive turns may exceed about 0.7 mm. In some embodiments, the distance between consecutive turns may be less than about 1.5 mm. In some embodiments particularly suitable for protection against pulmonary embolism, the distance between consecutive windings may be greater than about 1.5 mm.

In some embodiments, emboli originating upstream of the device may be filtered by the device because they cannot pass between consecutive turns. In this way the device provides embolic protection.

In some embodiment, the filament comprises a hollow lumen. This makes the filament more visible by ultrasound imaging, in some embodiments, the device may comprise one or more of: a radiopaque marker, an echogenic marker, a radioactive marker, a magnetic marker, and a magnetic resonance marker.

In some embodiments, the filament may be made of a metal, a plastic, a natural polymer, a shape memory alloy, a super-elastic alloy, a biodegradable material, a bioresorbable material or a bioabsorbable material.

In some embodiments, the device may comprise two or more filaments. The filaments may be joined at their ends. The filaments may each have a helical shape. The filaments may possess an equal phase offset with respect to each other. For example, an embodiment consisting of three filaments is possible in which consecutive filaments are mutually phase-offset by 120 degrees.

In some embodiments, embolic protection devices according to the present disclosure may be delivered using a delivery device comprising: a needle having a pusher slidable within the needle, a lumen, a sharp distal end, and an outer diameter less than about 1 mm.

In some embodiments, an embolic protection device is loaded in an undeployed state in the distal end of the delivery device. The pusher is loaded in the proximal end of the delivery device such that within the needle. The distal end of the pusher is in contact with the proximal end of the device. The delivery device is used to deploy the embolic protection device in a patient: A puncture is made in a wall of the target vessel using the sharp distal end of the needle or the distal end of the device; the device is exteriorized into the lumen of the vessel by pushing the pusher, retracting the needle, or both, such that the primary axis of the device ends up approximately perpendicular to the fluid flow in the vessel; and retracting the pusher and the needle from the patient.

In some embodiments, deployment of the device entails making a second puncture at a location on the vessel wall that is approximately diametrically opposed to the location of the first puncture.

In some embodiments, the device is anchored externally to the vessel at a location proximate the puncture. In some embodiments, the device is also anchored externally to the vessel at a location proximate to the second puncture.

In some embodiments, the device is implanted in any of an artery, a vein, an aorta, a common carotid artery, an internal carotid artery, a subclavian artery, a brachiocephalic artery, a renal artery, a vertebral artery, a superficial femoral vein, a deep femoral vein, a popliteal vein, an iliac vein, an inferior vena cava, and a superior vena cava.

In some embodiments, an implanted device may be retrieved from the implantation site. A retrieval apparatus according to some embodiments may comprise an extraction sheath and a grasper. The extraction sheath may have a sharp end, which is configured to pierce skin. The extraction sheath may also be configured to internalize the embolic protection device. The grasper may be configured to catch the proximal end of the implanted device and to fit inside the lumen of the extraction sheath. The retrieval apparatus may thus be used to extract the implanted device through the extraction sheath.

In some embodiments, embolic protection may be provided by ligating or occluding a target vessel. An occlusion or ligation device according to some embodiments may comprise an undeployed and a deployed state; a filament comprising a proximal segment and a distal segment, which are capable of being disconnected from each other at a separation point; a distal anchor disposed at the distal end; and a slidable proximal anchor. The proximal anchor is located in the undeployed state proximally to the separation point. In the deployed state the proximal anchor is located distally to the separation point. The filament may be separated into two parts by applying mechanical or electrical energy to the separation point.

In some embodiments, a system for occluding or ligating a target vessel may comprise the occlusion/ligation device, a push tube configured to slidably receive the proximal segment of the filament and to push the slidable proximal anchor over the filament towards the distal anchor, and a delivery catheter comprising a needle configured to slidably receive the push tube and the device.

In some embodiments, vessel occlusion or ligation may be brought about by: providing the ligation system; puncturing the vessel wall at two diametrically-opposed sites; retracting the needle away from the device allowing the distal anchor to engage tissue in its vicinity; further retracting the needle wherein the device is exteriorized within the lumen of the vessel, and, upon the needle being retracted to a point external to the vessel lumen, the proximal anchor engages tissue in its vicinity; sliding the proximal anchor towards the distal anchor, resulting in external compression of the vessel and adhering or bringing together the two opposing vessel walls; applying mechanical or electrical energy to the separation point, thereby separating the proximal part of the filament from the remainder of the device; and, retracting the proximal part of the filament from the patient.

Advantages of Some of the Embodiments

The following advantages are realized by one and/or another of the disclosed embodiments:
  providing embolic protection in patients unsuitable for anticoagulant drugs;
  obviating the need for anticoagulant drugs and their side-effects in patients at high risk for embolic disease;
  protection against emboli originating anywhere in the arterial circulation proximally to the neck, as opposed to left atrial appendage occluders that target emboli originating in the left atrial appendage alone;
  reduced risk of thrombus formation as compared to mesh-based devices: some embodiments according to the present disclosure have a thin monofilament body lacking wire crossings, thereby providing less resistance to blood flow, less flow obstruction and stagnation, and subsequent activation of the blood clotting cascade;
  reduced risk of clogging due to excessive endothelial cell growth as compared to tubular mesh based devices: some embodiments of the present disclosure have far less contact area with vessel walls;
  better physical fit to conform with changes ire vessel diameter because some embodiments according to the present disclosure have a helical design that is particularly good at coping with tensile and/or compressive forces;
  less invasive than embolic protection devices that are delivered by catheterization, and therefore, reduced risk of complications. For example, some embodiments may be delivered through a very thin needle having a diameter of less than about 0.5 mm as compared to catheters that have a diameter of about 2 mm. As a result, punctures made during the delivery of embodiments according to the present disclosure self-seal and self-heal, as opposed to the far larger and more traumatic catheter punctures;
  delivery is lower in cost and simpler. For example, embolic protection devices according to some embodiments may be implanted bedside under ultrasound guidance and do not require a catheterization laboratory, fluoroscopy, or highly skilled personnel;
  easily retrievable using minimally invasive technique, which does not require that the target vessel be punctured again.

BRIEF DESCRIPTION OF THE DRAWINGS

The invention may be better understood with reference to the accompanying drawings and subsequently provided detailed description:

FIGS. 1A and 1B respectively depict undeployed and deployed states of a monofilament filtering device according to some embodiments of the present disclosure.

FIGS. 4A and 4B respectively depict undeployed and deployed states of an end piece according to some embodiments of the present disclosure.

FIGS. 8A and 8B respectively depict undeployed and the deployed states of an embolic protection device comprising more than one filament according to some embodiments of the present disclosure.

FIG. 8C is a cross-sectional view of the deployed state of the embolic protection device of FIGS. 8A and 8B.

FIGS. 10A-10E depict a system and method according to some embodiments of the present disclosure, which are intended for implanting a monofilament filtering device according to some embodiments of the present disclosure.

FIGS. 11A-11D depict a system and method according to some embodiments of the present disclosure, which are intended for implanting another monofilament filtering device according to some embodiments of the present disclosure.

FIGS. 13A-13F depict a method according to some embodiments of the present disclosure, which is intended for retrieving a filtering device according to some embodiments of the present disclosure.

DETAILED DESCRIPTION OF SOME OF THE EMBODIMENTS

Figure 1D:
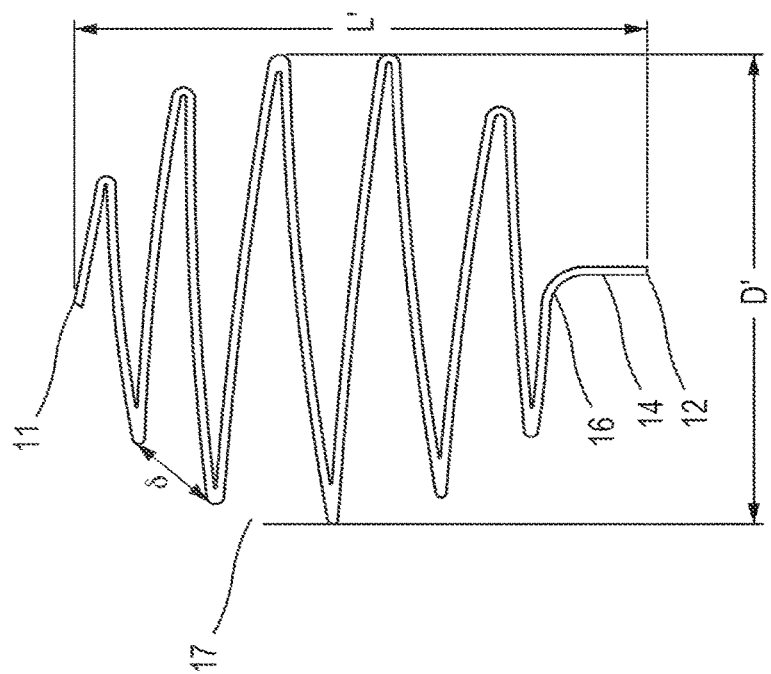
FIGS. 1C and 1D respectively depict undeployed and deployed states of a monofilament filtering device according to some embodiments of the present disclosure, which lack the distal-most turn and segment of the device of FIG. 1B.

Reference is now made to FIG. 1A, which depicts some embodiments of an undeployed state of a filtering device (embolic protection device) of the present disclosure. Filtering device 10, configured to be implanted in a body vessel, can be a filament of cylindrical shape. However, cross sectional shapes other than circular are also possible.

In some embodiments, the length of the filament from which filtering device 10 is made may be greater than the diameter of the body vessel for which it is intended. Thus, if implanting the filtering device in a vein or an artery having a diameter of about 7 mm, then the length of the filament may be, for example, in the range of about 7 to about 300 mm.

In some embodiments, the diameter of the filament from which filtering device 10 is made may be substantially less than its length. For implantation into a blood vessel, the filament diameter may be chosen of a size sufficient so as to not cause blood coagulation. Therefore, the filament diameter, according to some embodiments, is less than about 0.5 mm, and more specifically less than about 0.2 mm, and even more specifically, less than about 0.15 mm.

In some embodiments, an undeployed state of device 10 may assume, or be constrained to assume, any shape that fits within the lumen of a tube having a length L and an inner diameter D such that L is much greater than D. (the terms "substantially linear" or "substantially straight" as used herein refer to all such shapes.) For example, length L may be in the range of about 10 to about 300 mm, whereas the diameter D may be in the range of about 0.05 to about 0.7 mm.

In some embodiments, an undeployed state of device 10 may assume, for example, the shape of a substantially straight line, as in FIG. 1A. In some embodiments, a portion or a segment of the device, but not the entire device, in the undeployed state may assume, or be constrained to assume, the shape of a substantially straight line. It may also assume, or be constrained to assume, a shape resembling a helix in which the pitch (that is, the vertical distance between consecutive windings) may be much larger than the helix diameter (that is, the diameter of the smallest cylinder in which the helix might fit).

Reference is now made to FIG. 1B which depicts an embodiment of the deployed state of a filtering device of the present disclosure. In the deployed state, filtering device 10 may assume the shape of a helix (spring or spiral). This helix shape may have windings or turns that vary in diameter. The windings may, but do not have to, approximately trace the shape of a spherical shell. The helix shape possesses a primary axis, which may roughly-coincide with the axis of the helix.

More generally, the deployed state of the device may trace any shape resembling, or residing in the shell of, a body of revolution. A body of revolution is defined by revolving a plane shape around an axis in the plane. By the "primary axis" of the deployed shape of the device, in some embodiments, it is meant to be a line roughly coinciding with this axis in the plane. For example, whenever the deployed shape of the device has the helical shape of FIG. 1B, the primary axis roughly coincides with the axis of the helix.

In some embodiments, having the deployed shape of the device resemble, or reside in the shell of, a body of revolution has the advantage that no control of the orientation of the device around the primary axis need be maintained during implantation. This makes for a robust, simple, and reproducible implantation procedure.

The deployed length L' of filtering device 10 may be greater than the diameter of the body vessel for which it is intended. Thus, if implanting the filtering device in a vein or an artery having a diameter of about 7 mm, then the deployed length L' may be, for example, in the range of about 7 to about 20 mm. The deployed diameter D' of filtering device 10 may be less than or approximately equal to the diameter of the target vessel at the implantation site. For example, if implanting the filtering device in a vein or an artery having a diameter of about 7 mm then the diameter D' may be in the range of about 5 mm to about 8 mm.

In some embodiments, in the deployed state, the primary axis roughly coincides with the line segment connecting distal end 11 and proximal end 12 of device 10. The primary axis may be substantially perpendicular to the plane approximately defined by some of the helix turns or windings. The distal segment 13 and the proximal segment 14 of device 10 may be substantially collinear with the primary axis.

The distal turn 15 of device 10 may reside in a plane containing the primary axis. Likewise, the proximal turn 16 in device 10 may also reside in a plane containing the primary axis. The two planes may, but do not have to, be one and the same. All of the remaining turns in device 10 may reside in planes that are approximately, but not necessarily exactly, perpendicular to the primary axis.

Device 10 may be configured such that in the deployed state the radius of curvature at any point along its length is greater than or equal to a critical value $R_c$. This critical value may be assigned such that the strain suffered at any point of device 10 is less than or equal to the critical strain required to bring about an elastic-to-plastic transformation upon transition from the deployed to the undeployed state. In this way device 10 may be able to transition from the deployed shape to the undeployed shape and back without substantial difference between the initial and final deployed shapes. For example, if the filament from which device 10 is made has a circular cross section having diameter d, and the material from which device 10 is made has critical strain $\varepsilon$, then the critical value $R_c$, is given by $R_c = d/2\varepsilon$. Therefore, if, for example, device 10 is made from super-elastic nitinol having critical strain $\varepsilon$ of about 0.08, and the filament diameter d is about 0.15 mm, then the critical radius of curvature will be roughly about 0.94 mm.

Accordingly, the deployed state of device 10 may be configured to trap embolic material having typical size that is larger than the distance $\delta$ between consecutive windings. Whenever device 10 is configured to protect a patient from major embolic stroke, device 10 is made to trap emboli exceeding about 1-2 mm in size. In this case the distance $\delta$ may be less than about 1.5 mm, and, more specifically, in the range of about 0.7 mm and about 1.5 mm. Even more specifically, the distance $\delta$ may reside in the range of about 0.3 mm and about 1.2 mm. Whenever device 10 is configured to protect a patient from pulmonary embolism, device 10 may be made to trap emboli exceeding about 5 mm in size. In this case the distance $\delta$ may be less than about 3 mm, and, more specifically, in the range of about 1.5 mm and about 5 mm.

Filtering device 10 may be configured to be relatively stiff or, in some embodiments, relatively flexible. Alternatively, filtering device 10 may be configured to assume any degree of flexibility. In the deployed shape, filtering device 10 may possess either a low spring constant or a high spring constant. Alternatively, in the deployed state, filtering device 10 may be configured to any value for its corresponding spring constant.

Filtering device 10, according to some embodiments, may be configured as a solid filament. Alternatively, it may be configured as a tube having a hollow lumen, or as a tube having its ends closed-off, thereby leaving an elongated air-space inside filtering device 10. Leaving an air-space inside filtering device 10 may have the advantage of making filtering device 10 more echogenic and therefore more highly visible by ultrasound imaging. Filtering device 10 may possess one or more echogenic marker and/or one or more radiopaque marker anywhere along its length.

Filtering device 10 may be made from any suitable biocompatible material, such as metal, plastic, polymers, or natural polymer, or combination thereof. Suitable metals include (for example): steel, stainless steel (e.g., 305, 316 L), gold, platinum, cobalt chromium alloys, shape memory and/or super-elastic alloys (e.g., nitinol), titanium alloys, tantalum, or any combination thereof. Suitable plastics include (for example) silicones, polyethylene, polytetrafluoroethylene, polyvinyl chloride, polyurethane, polycarbonate, and any combination thereof. Suitable polymers include shape memory polymers or super-elastic polymers. Suitable natural polymers may include collagen, elastin, silk and combinations thereof.

In some embodiments, filtering device 10 may be made from an absorbable, biodegradable, or bioresorbable material, such as a bioresorbable polymer or a bioresorbable metal. Suitable bioresorbable polymers include polyL-lactide, polyD,L-lactide, polyglycolide, poly ε-caprolactone, 50/50 D,L lactide/glycolide, 82/18 L-lactide/glycolide, 70/30 L-lactide/ε-caprolactone, 85/15 L-lactide/glycolide, 10/90 L-lactide/glycolide, 80/20 L-lactideD,L-lactide, or any combination thereof. Suitable bioresorbable metals can include magnesium alloy.

Some embodiments of filtering devices according the present disclosure are substantially similar to filtering device 10, except for one or more of the following differences: part or all of distal segment 13 may be lacking, part or all of distal turn 15 may be lacking, part or all of proximal segment 14 may be lacking, and part or all of proximal turn 16 may be lacking.

Figure 1C:
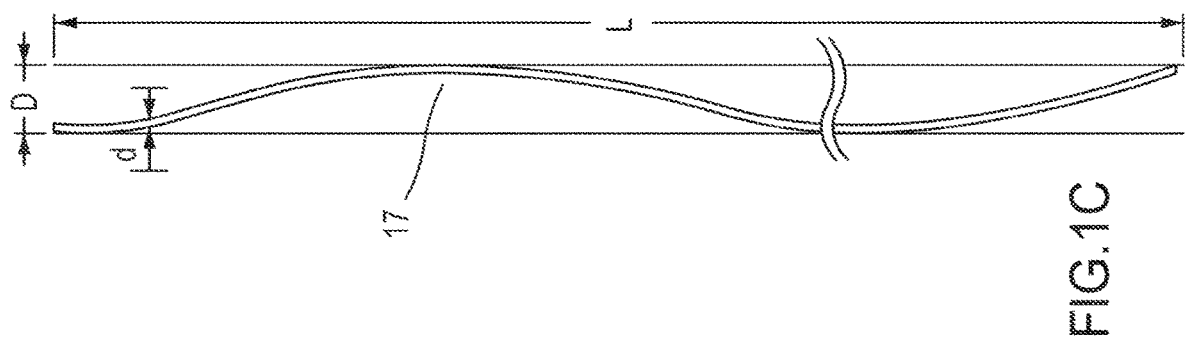

For example, FIG. 1C depicts an undeployed state and FIG. 11D depicts a deployed state of a filtering device 17 substantially similar to filtering device 10 but lacking distal segment 13 and distal turn 15. Device 17 may be particularly suitable for implantation through a single puncture in a target vessel. In such an embodiment, all device parts except perhaps for proximal segment 14 and proximal end 12 may lie entirely inside the vessel lumen or walls. Distal end 11 may comprise a non-traumatic tip (such as, for example, a polished ball), configured to safely appose the inner wall of the vessel, or a short, sharp end configured to anchor in the vessel wall without breaching it completely.

The helical portion of device 17 may have a length that is shorter, the same as, or longer than the diameter of the vessel for which it is intended. A longer length may facilitate apposition of the distal end of the device against the vessel wall. A shorter length may have the advantage of minimizing contact between the device and the vessel wall.

Figure 2B:
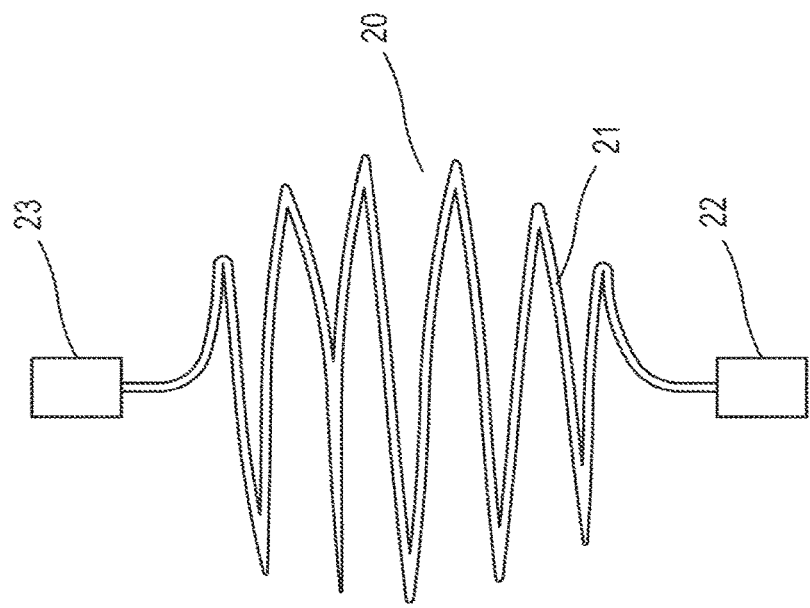
FIGS. 2A and 2B respectively depict undeployed and deployed states of a monofilament filtering device including end pieces according to some embodiments of the present disclosure.
Figure 2A:
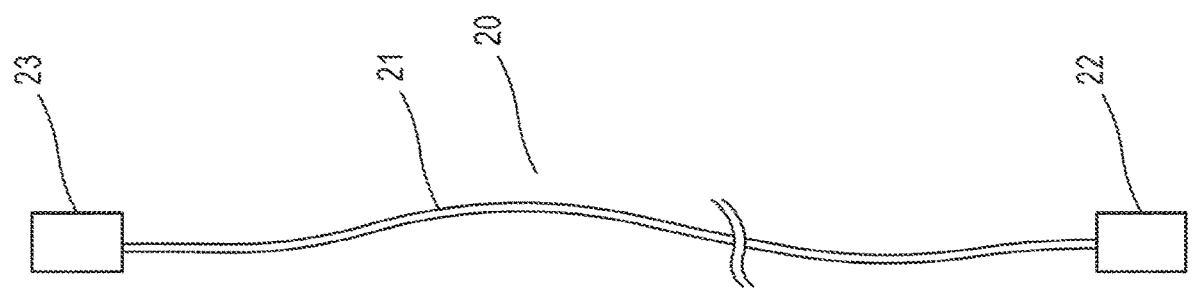

Reference is now made to FIGS. 2A and 2B, which respectively represent undeployed and deployed states of another embodiment of the filtering device of the present disclosure. Filtering device 20 is substantially similar to filtering device 10 of FIGS. 1A and 1B: device 20 comprises a filament 21 that is substantially similar to the filament from which device 10 is made. However, device 20 may also comprise one or more of a first end piece 22 residing at one end of filament 21, and a second end piece 23 residing at the opposite end of filament 21.

In an undeployed state (FIG. 2A), filtering device 20, including end-pieces 22 and 23, may be configured to reside in the lumen of a hollow needle. Upon exteriorization from such a needle (FIG. 2B), filtering device 22 may assume a deployed shape substantially similar to that of filtering device 10, and end-pieces 22 and 23 may, but do not have to, assume a shape that is different from their shape in the undeployed state of device 20.

Figure 2D:
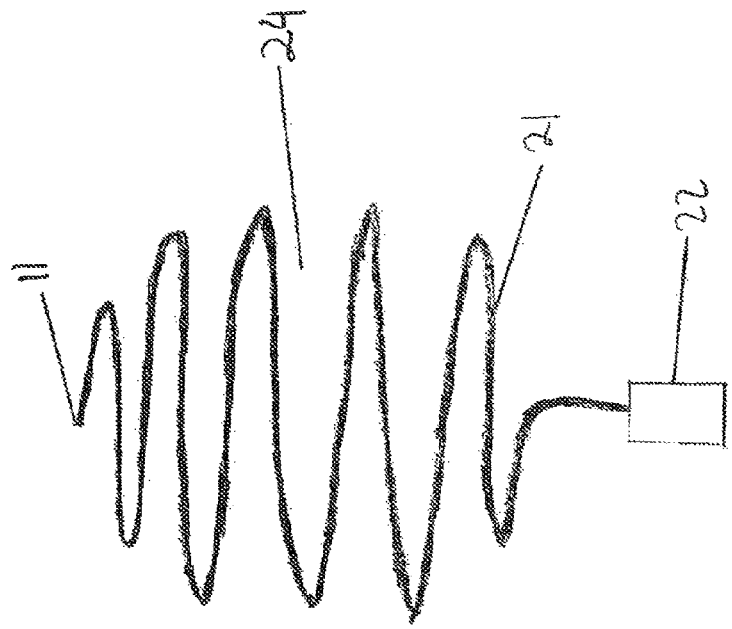
FIGS. 2C and 2D respectively depict undeployed and deployed states of a monofilament filtering device including an end piece and lacking the distal-most turn and segment of the device of FIG. 2B, according to some embodiments of the present disclosure.
Figure 2C:
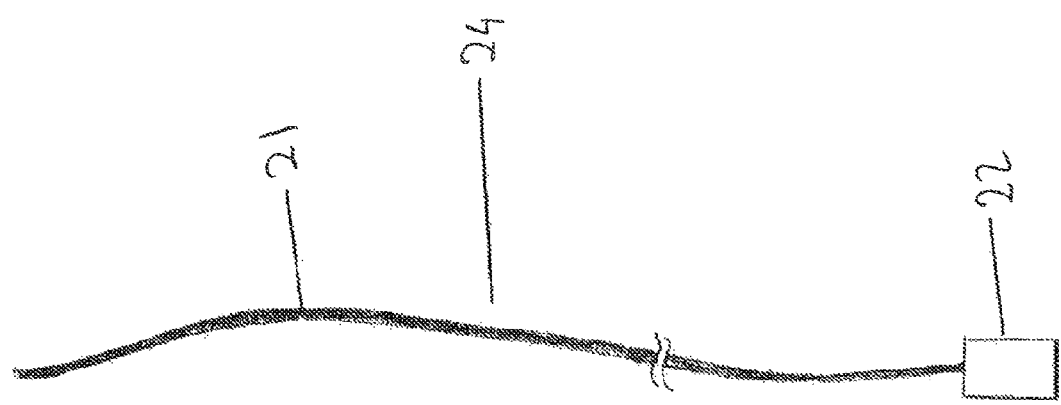

Reference is now made to FIGS. 2C and 2D, which respectively represent undeployed and deployed states of another embodiment of the filtering device of the present disclosure. Filtering device 24 is substantially similar to filtering device 17 of FIGS. 1C and 1D device 24 comprises a filament 21 that is substantially similar to the filament from which device 17 is made. However, device 24 may also comprise an end piece 22 residing at its proximal end.

In an undeployed state (FIG. 2C), filtering device 24, including end-piece 22, may be configured to reside in the lumen of a hollow needle. Upon exteriorization from such a needle (FIG. 2D), filtering device 24 may assume a deployed shape substantially similar to that of filtering device 17, and end-piece 22 may, but does not have to, assume a shape that is different from its shape in the undeployed state of device 24.

Figure 3B:
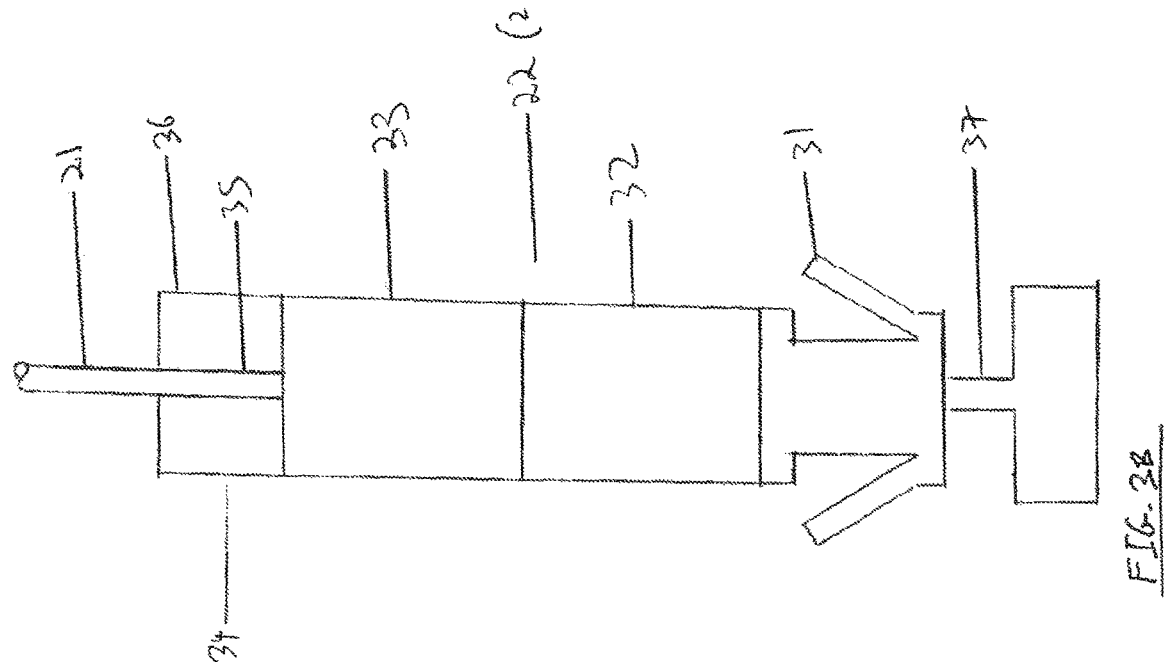
FIGS. 3A and 3B depict a schematic rendering of undeployed and deployed states of an end piece according to some embodiments of the present disclosure.
Figure 3A:
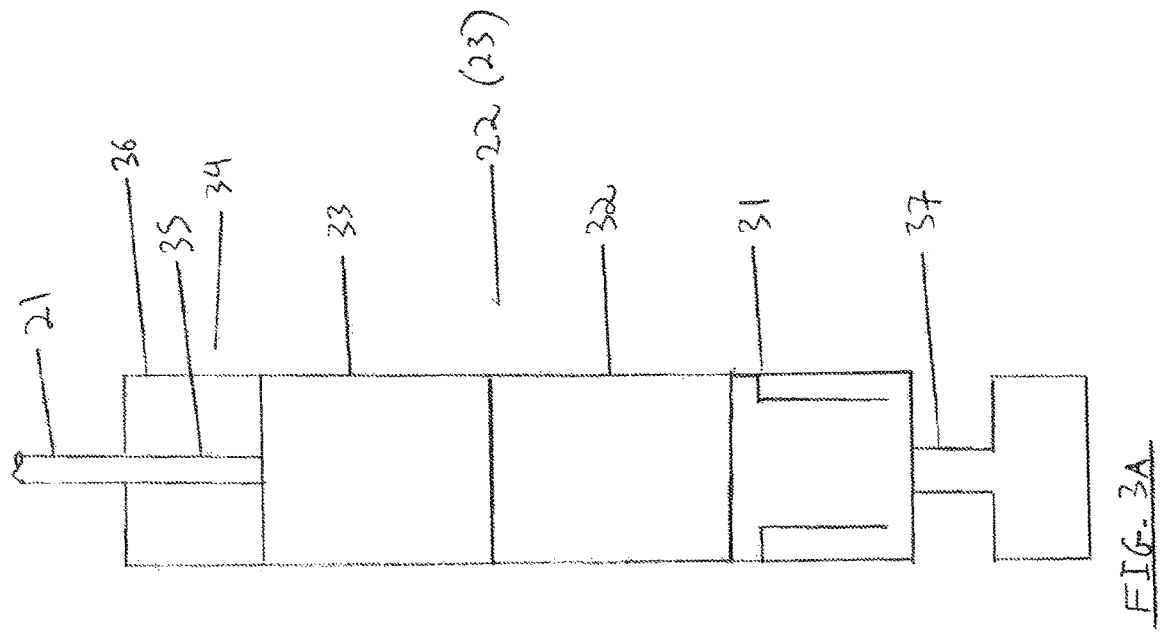

Reference is now made to FIG. 3A, which depicts the undeployed state and the components that each of end pieces 22 and 23 may separately comprise. End pieces 22 and 23 may each separately comprise one or more of the following: an anchor 31, a radiopaque marker 32, an echogenic marker 33, a hearing 34, and a retrieval knob 37. End pieces 22 and 23 may each also separately comprise a non-traumatic tip, such as a ball-shaped protrusion made of metal. End pieces 22 and 23 may also each separately comprise one or more of a radioactive marker, a magnetic marker, and a magnetic resonance marker.

End pieces 22 and 23 may each separately be integral with filament 21. They may be made to assume undeployed and deployed shapes that are different. For example, the deployed shape may comprise loops or turns configured to anchor device 24 in tissue. Anchor 31 may comprise any means known in the art for attaching a foreign body to living tissue. For example anchor 31 may comprise a roughened surface, a bulge, a mass, one or more barbs, one or more micro-barbs, one or more hook, a hydrogel bulge configured to enlarge upon contact with an aqueous environment, or their likes. Anchor 31 may, but does not have to, be configured to change its shape upon transition from the undeployed state to the deployed state of devices 20 or 24 (FIG. 3B). Anchor 31 may comprise a biocompatible metal, a biocompatible polymer, a shape memory material, a super elastic material (e.g. super elastic nitinol) or any combination thereof.

Whenever anchor 31 is of the shape-changing variety, it may be made, for example, of a super elastic material, in its free state, that is, in the state in which no (or little) force is exerted on it by its external environment, the anchor will assume the deployed state depicted in FIG. 3B. Whenever anchor 31 is housed in, for example, a hollow needle of a sufficient bore, its moving parts will retain sufficient elastic energy as to cause them to assume their deployed shape upon release. Thus, upon exteriorization from the needle at the implantation site, anchor 31 will transition from its undeployed state of FIG. 3A, to the deployed state of FIG. 3B.

Radiopaque marker 32 may comprise a biocompatible radiopaque material, such as gold or platinum.

Echogenic marker 33 may comprise a biocompatible echogenic material, such as tantalum. The marker 33 may comprise an echogenic coating comprising air micro-bubbles, cornerstone reflectors, or any other means known in the art to increase echogenicity. Upon transition from the undeployed state to the deployed state of device 20 or device 24, marker 33 may retain its shape. Alternatively, the shape of marker 33 may change upon transition from the undeployed to the deployed state.

Bearing 34 may comprise an axle 35 and a housing 36. Axle 35 may be configured to freely rotate within housing 36. Alternatively, axle 35 may be configured to rotate within housing 36 with any pre-specified degree of friction. Axle 35 may be rigidly connected to an end of filament 21. Alternatively, axle 35 may be integral with an end of filament 21. Housing 36 may be rigidly connected to anchor 31. In this way, upon application of torque to axle 35, the axle may rotate inside housing 36, and housing 36 may remain substantially motionless with respect to the tissue in which it resides.

Bearing 34 may comprise any mechanism known in the art for constraining relative motion between the axle and the housing to only a desired motion. For example, bearing 34 may comprise a plain bearing, a bushing, a journal bearing, a sleeve bearing, a rifle bearing, a rolling-element bearing, a jewel bearing, and a flexure bearing.

Embodiments comprising a retrieval knob for, for example, other graspable means, such as a bulb, a loop, or a protrusion) are particularly suited for temporary or permanent implantation, whereas embodiments lacking a retrieval knob are particularly suited for permanent implantation, Retrieval knob 37 is any contraption capable of being grasped by grasping devices such as a grasper, a hook, or a snare. Retrieval knob 37 may be, for example, a bulb, a loop, or a protrusion. It may be made from a plastic, a metal, a natural polymer, or a biodegradable polymer. Knob 37 may be configured to be grasped by any retrieval mechanism capable of connecting to the knob and applying force to the knob so as to cause the retrieval of a device comprising it, such as 20 or 24, from the tissue in which it is deployed. Suitable retrieval mechanisms include, for example, graspers, hooks and snares.

Figure 5B:
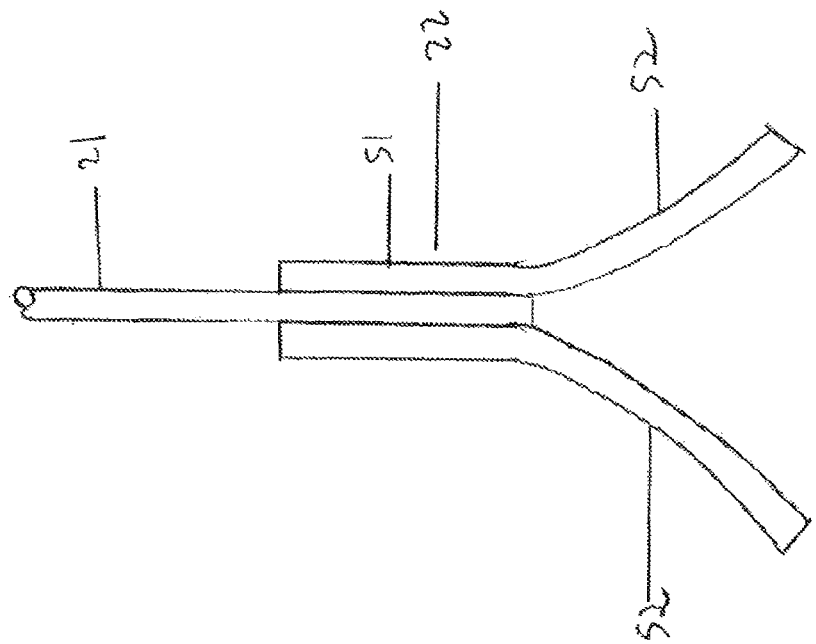
FIGS. 5A and 5B respectively depict undeployed and deployed states of another end piece according to some embodiments of the present disclosure.

We note that different components in each end piece need not be physically distinct: for example, the housing of the bearing may also serve as an anchor, the radiopaque marker and the echogenic marker may be one and the same, the hearing may serve to provide radiopacity or echogenicity, and so forth. To illustrate this point, reference is now made FIGS. 4A and 4B, which represent an embodiment of end piece 23 according to the present disclosure, and to FIGS. 5A and 5B, which represent an embodiment of end piece 22 according to the present disclosure.

FIG. 4A depicts an undeployed state of a particular embodiment of end piece 23, according to the present disclosure. End piece 23 may comprise an external cylinder 41, prongs 45, a proximal ring 42, a distal ring 43, a hall 44, and axle 35. External cylinder 41 and prongs 45 may be integral with each other. They may be made from a shape memory or super-elastic alloy, such as nitinol. Upon transition of, for example, device 20 from the undeployed to the deployed state, prongs 45 extend outwards, thereby anchoring end piece 23 in the tissue in which it is implanted. The proximal part of cylinder 41, proximal ring 42, and distal ring 43 may be rigidly connected to each other to form a bearing housing 36. Rings 42 and 43 may each be made from a radiopaque and or echogenic material, such as gold, platinum, or tantalum. The end of filament 21 may be rigidly connected to, and may be integral with, ball 44, which may be made from metal, a polymer, an alloy, a shape memory material, or a super elastic material. Together, the end of filament 21 and ball 44 provide a bearing axle 35. The axle 35 is free to rotate within housing 36 more or less around the housing's principal axis. However, in some embodiments, rings 42 and 43 substantially prevent all other relative motions of axle 35 with respect to housing 36. Housing 36 and axle 35 together provide a bearing.

Figure 5A:
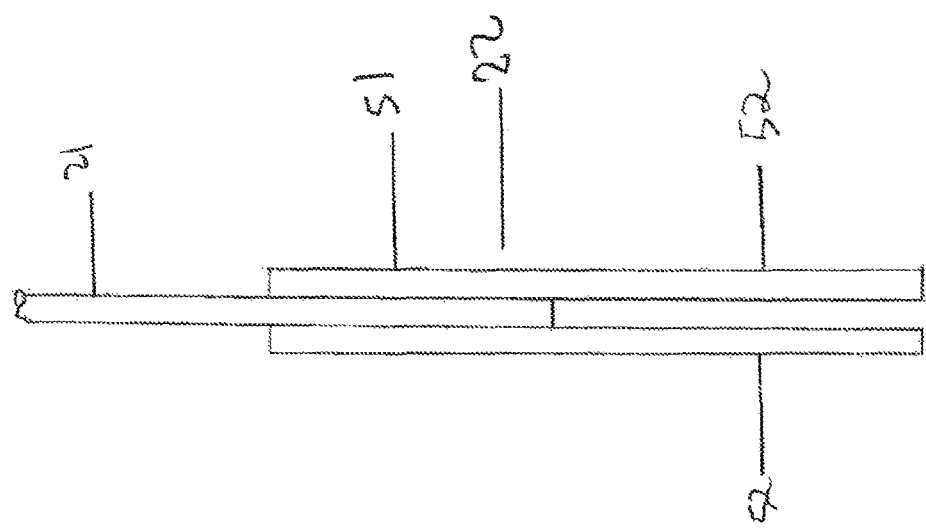

FIG. 5A depicts an undeployed state of some embodiments of end piece 22, according to the present disclosure. End piece 22 may comprise an external cylinder 51, and prongs 52, which may be integral with the cylinder. Both the prongs and the cylinder may be made from a shape memory or super-elastic material, such as nitinol. External cylinder 51 may be rigidly connected to the end of filament 21 using any connection means known in the art, such as crimping, welding, soldering, gluing, and their likes. The external surface of cylinder 51 may be coated with an echogenic coating, or carry cornerstone reflectors. In this way, end piece 22 may comprise an anchor and an echogenic marker. However, the embodiment of end piece 22 presented in FIGS. 5A and 5B does not comprise a bearing or a retrieval knob.

Figure 6B:
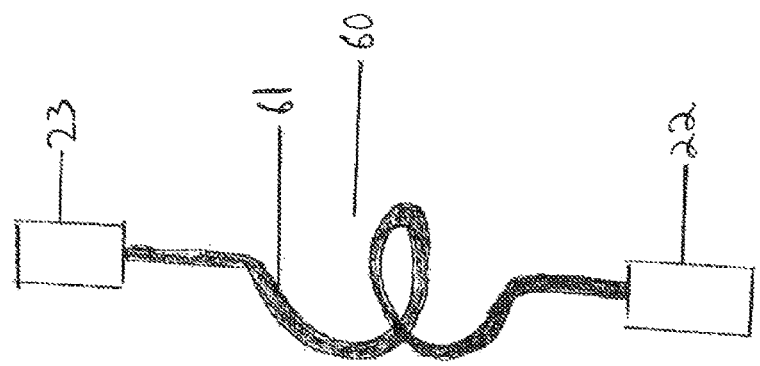
FIGS. 6A and 6B respectively depict undeployed and deployed states of a spring-shaped monofilament embolic protection device including two end pieces according to some embodiments of the present disclosure.
Figure 6A:
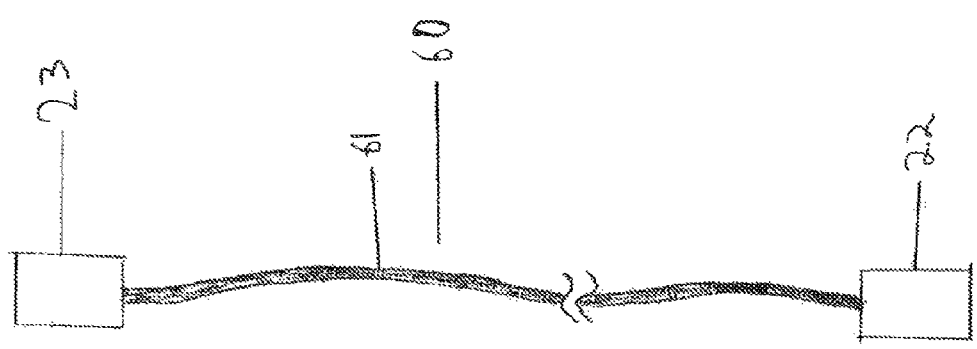

Reference is now made to FIGS. 6A and 6B, which depict undeployed and deployed states, respectively, of an embolic protection device according to some embodiments of the present disclosure. Device 60 is substantially similar to device 17. Filament 61 assumes a spring shape in the deployed state. The spring coils of device 60 need not reside in geometrical planes that are approximately perpendicular to the primary axis of the device (the line connecting end pieces 22 and 23). In addition, the coils of device 60 need not trace the shape of a spherical shell. Embodiments in which the diameter of the spring shape traced by the device are less than the diameter of the vessel for which it is intended are possible, thereby minimizing vessel wall contact. Such embodiments may be well suited for implantation in veins for the purpose of preventing pulmonary embolism: the dangerous emboli are fairly large (>5 mm in diameter, >10 mm in length). Thus, efficient capture of emboli is possible even if filament 61 has little or no wall contact throughout its length.

The spring shape of filament 61 may accommodate large changes in the diameter of the vessel for which it is intended by allowing filament 61 to lengthen or shorten in accordance with the growth or shrinkage in vessel diameter. This is particularly important when device 60 is implanted in a peripheral vein, such as a femoral vein, which may dilate by up to a factor of two in response to, for example, Valsalva maneuver.

Figure 6D:
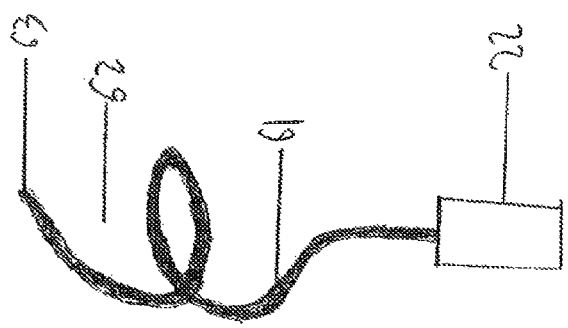
FIGS. 6C and 6D respectively depict undeployed and deployed states of a spring-shaped monofilament embolic protection device having one end piece according to some embodiments of the present disclosure.
Figure 6C:
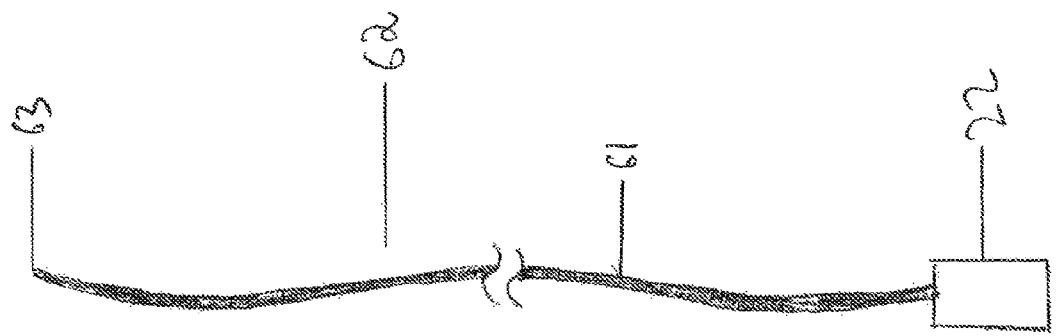

Reference is now made to FIGS. 6C and 6D, which respectively depict undeployed and deployed states of a filtering device 62 substantially similar to filtering device 60, but lacking end piece 23. Device 62 may be particularly suitable for implantation through a single puncture in a target vessel. In such an embodiment, all device parts except perhaps for proximal end piece 22 may lie entirely inside the vessel lumen or walls. Distal end 63 may comprise a non-traumatic tip (such as, for example, a polished ball), configured to safely appose the inner wall of the vessel, or a short, sharp end configured to anchor in the vessel wall without breaching it completely.

Figure 7C:
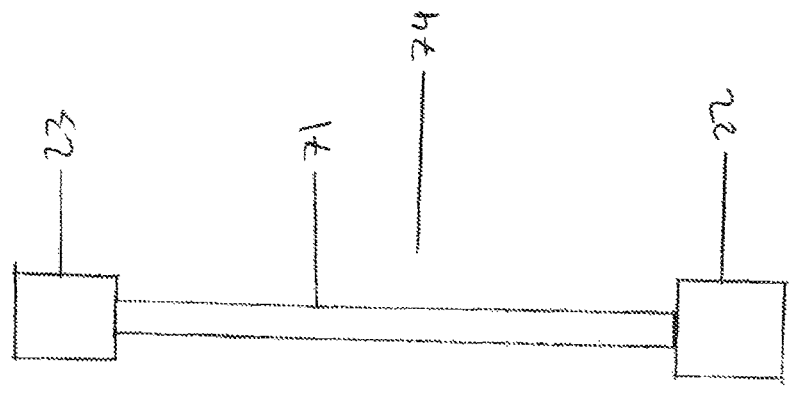
FIGS. 7A-7C depict straight monofilament embolic protection devices respectively including zero, one, and two end pieces according to some embodiments of the present disclosure.
Figure 7B:
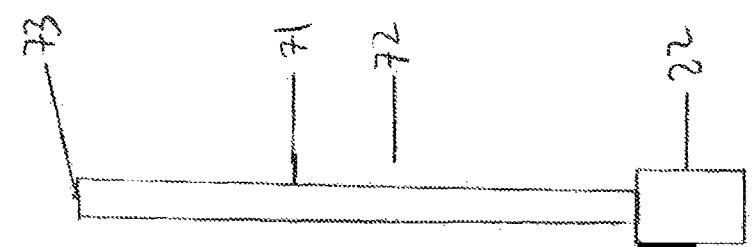
Figure 7A:
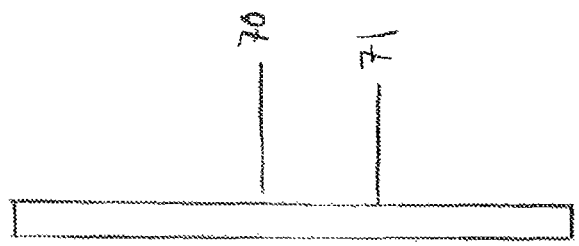

Reference is now made to FIGS. 7A-7C, which depict embodiments of an embolic protection device according to some embodiments of the present disclosure. These embodiments are particularly suitable for implantation in locations where bisecting a vessel's cross section into two roughly equal halves can result in adequate embolic protection. For example, the devices of FIGS. 7A-7C may be implanted in a leg vein in order to prevent deep vein thrombi from embolizing to the lungs. They may also be implanted, for example, in a vertebral artery supplying blood to the posterior brain circulation, thereby preventing emboli traveling to the brain through the vertebral artery from causing posterior circulation stroke.

Device 70 of FIG. 7A comprises is a filament 71 that may be substantially similar to the filament of device 10 in terms of diameter, flexibility, structure (solid or hollow), and material composition. Filament 71 may have a fixed or a variable diameter along its length. The length of device 70 may be greater, roughly the same as, or smaller than the diameter of the vessel in which it is implanted. The attribute that distinguishes device 70 over device 10 is this: device 70 is substantially straight in both its undeployed and its deployed states.

Device 72 of FIG. 7B is substantially similar to device 70, except for the following major difference: device 72 comprises in addition to filament 71 an end piece 22. End piece 22 may be situated at the proximal end of filament 71, and may be integral with it. Alternatively, end piece 22 and filament 71 may be joined by any chemical, physical, or mechanical means known in the art, such as gluing or crimping. End piece 22 may comprise one or more of an anchor, an echogenic marker, a radiopaque marker, and a retrieval knob. Distal end 73 of device 72 may be sharpened as to be suitable for creating punctures in tissue. Distal end 73 may also comprise a non-traumatic tip.

Device 74 of FIG. 7C is substantially similar to device 70, except for the following major difference: device 74 comprises in addition to filament 71 an end-piece 22 at one of its ends and an end piece 23 at its opposite end. End pieces 22 and 23 may each be integral with filament 71, or each may be joined to filament 71 by any chemical, physical, or mechanical means known in the art, such as gluing or crimping. End pieces 22 and 23 may each separately comprise one or more of an anchor, an echogenic marker, a radiopaque marker, and a retrieval knob.

Reference is now made to FIGS. 8A-8C. FIG. 8A depicts an embodiment 80 of the filtering device of the present disclosure. Filtering device 80 may comprise a filter body 83 and ends 81 and 82. Filter body 83 may comprise three filtering filaments 84, 85, and 86. FIG. 8A depicts filtering device 80 at its undeployed state. In this state, filtering device 80 is configured to fit in the lumen of a hollow needle, where its shape is constrained by the force applied by the walls of the needle. FIG. 8B depicts filtering device 80 in its deployed state. Because in the deployed state there is little force to constrain the filtering filaments to their collinear configuration of FIG. 8A, the filtering filaments 84, 85, and 86 come apart, assuming a cross sectional configuration as in FIG. 8C.

Elongated filtering element 80 may be made of a shape memory alloy, a shape memory polymer, a metal, a polymer, a biodegradable, bioabsorbable, or bioresorbable polymer, or a biodegradable, bioabsorbable, or bioresorbable metal. Each of the ends 81 and 82 of filtering device 80 may be unitary with filter body 83, or may be distinct, such as end pieces 22 and 23 as described above.

Filter body 83 of filtering device 80 is not limited to include any particular number of filtering filaments. Any number of filaments is possible, and an embodiment having three filtering filaments was presented above only as a representative example. Two, four, five, and six (or higher) filament configurations are also possible. Connection points and connecting bridges between distinct filtering filaments and across different points in the same filament are also feasible. An embodiment in which each filament by itself assumes the shape of a spring or a coil is feasible. Thus, an embodiment comprising, for example, three helix-shaped filaments, wherein the second helix is rotated with respect to the first helix by 120 degrees and the third helix is rotated with respect to the first helix by 240 degrees is feasible. A "bird's nest" design, in which one or more filtering filament is "multiply entangled" when in the deployed state, is also possible. A net-shape, such as a basket-shaped like a fishing net is also possible. A central filament centered in a ring, with the ring being configured to appose the vessel wall, is also possible.

In yet another embodiment of the present disclosure, the filtering device has one or more protrusions extending from a main branch filament, such that one or more side branches are formed (for example). These protrusions may have the form of free ends (brush like) or closed shapes with both ends connected to the main branch filament. In some embodiments, there are one or more end piece, such as end pieces 22 and 23, located at the distal and proximal ends of the filament.

The filtering devices of the present disclosure and their components may be manufactured, for example, by industrial processes known in the art, comprising one or more of the following: injection molding, extrusion, forming on a mandrel, heat treatment, and surface treatment.

Figure 9A:
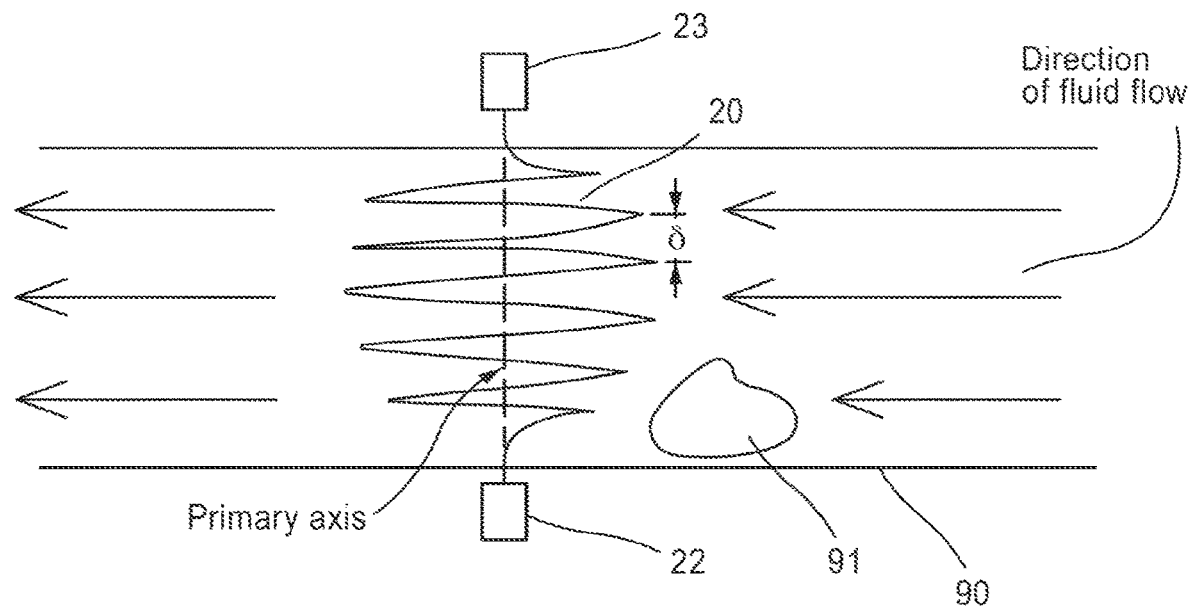
FIGS. 9A and 9B depict a monofilament filtering device in operation, according to some embodiments of the present disclosure.
Figure 9B:
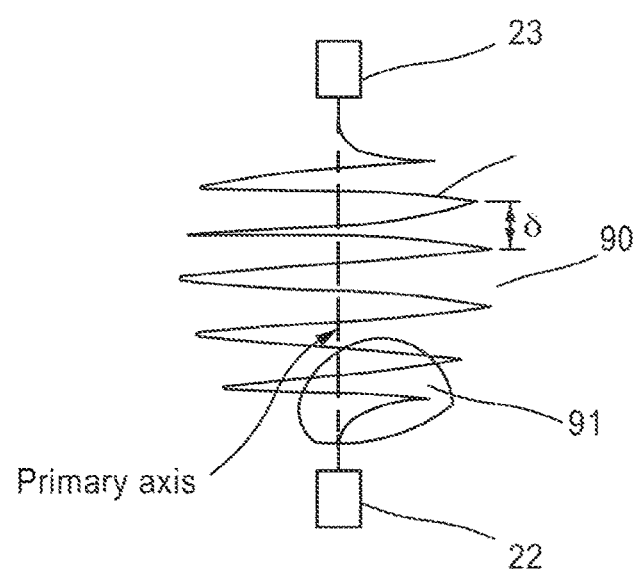

Reference is now made to FIGS. 9A and 9B, which respectively depict a side view and a cross-sectional view of a body vessel in which device 20 is implanted and operating. Device 20 is implanted in body vessel 90 such that its primary axis, that is, the axis extending from end piece 22 to end piece 23, is approximately perpendicular to the longitudinal axis of vessel 90, and roughly bisects a perpendicular cross section of the vessel. Whenever vessel 90 contains a flowing fluid, the primary axis of device 20 will be approximately perpendicular to the direction of fluid flow (and to the longitudinal axis of the vessel). Thus, if, for example, vessel 90 is an artery or a vein, the primary axis of device 20 will be approximately perpendicular to the direction of blood flow.

Embolus 91 is stopped by device 20 whenever its size is too large to pass through the openings defined by device 20 and the lumen of vessel 90. This size exclusion mechanism enables device 20 to protect various end-organs supplied by vessel 90 from embolic damage. For example, if vessel 90 is an artery supplying the brain, such as, for example, an aorta, a common carotid artery, an internal carotid artery, a subclavian artery, a brachiocephalic artery, or a vertebral artery, device 20 may protect the brain from stroke. If vessel 90 is a deep vein then device 20 may protect the lungs from pulmonary embolism.

The principle of operation (embolic protection) of embodiments 10, 17, 24, 60, 62, 70, 72, 74, and 80, as well as all other embodiments mentioned above, is substantially the same as for device 20: all devices are implanted such that their primary axis is roughly perpendicular to the direction of fluid flow in the target vessel, and the primary axis approximately divides a perpendicular cross section of the vessel to approximately equal halves. Emboli too big to pass through openings defined by the device and the vessel lumen are filtered by size exclusion.

Reference is now made to FIGS. 10A-10E, which illustrate a system and a method for providing embolic protection according to some embodiments of the present disclosure. The system and method are particularly suitable for delivering a filtering device 20 comprising at least one end piece incorporating a bearing. The at least one end piece incorporating a bearing enables torsion in filament 21 of device 20 to be controllably released during device implantation, thereby providing for a controlled and robust implantation procedure. However, the system and method of FIGS. 10A-10E do not require that at least one end-piece of device 20 comprise a bearing: they are suitable also for embodiments of device 24) that lack a bearing.

Figure 10A:
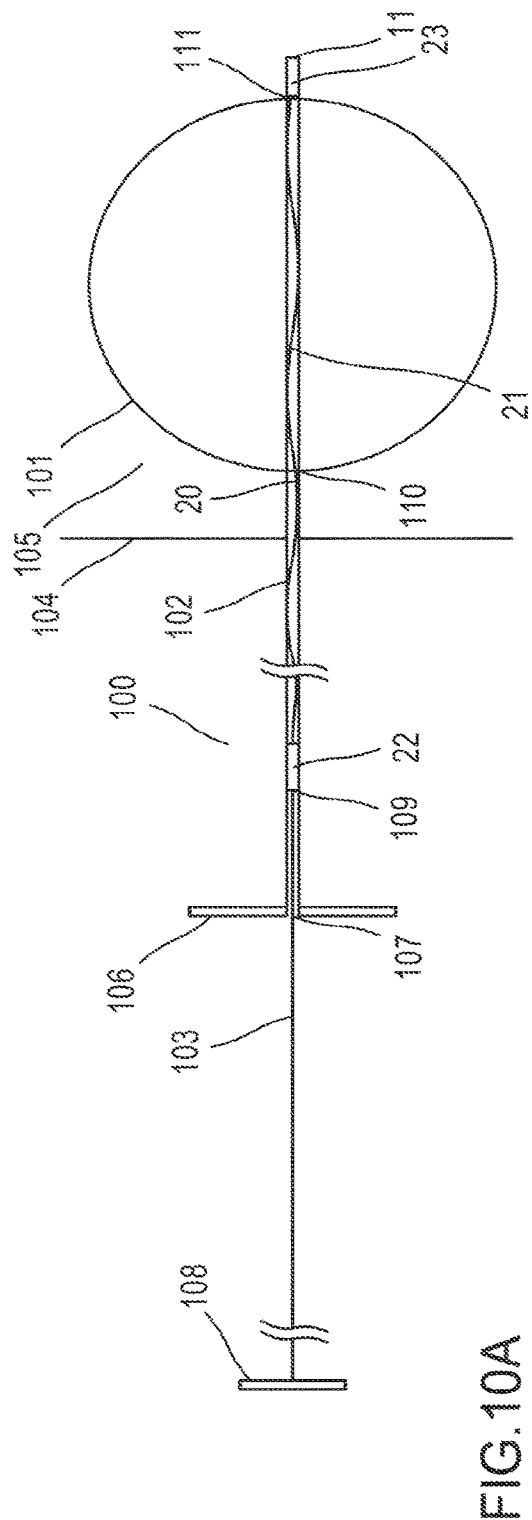

FIG. 10A depicts a system 100 configured to implant a filtering device 20 in a body vessel 101. System 100 comprises a hollow needle 102, a pusher 103, and filtering device 20. Taken together, the hollow needle and the pusher can be a delivery device. Hollow needle 102 has a sharp end 112 configured to pierce skin 104, subcutaneous tissue 105, and body vessel 101 of a patient. Needle 102 may have a needle handle 106 located at its proximal end 107. The needle handle 106 may be rigidly connected to needle 102. Pusher 103 may have a pusher handle 108 located at its proximal end.

Hollow needle 102 may have a very small inner and outer diameter. For example, if the maximal collapsed diameter of undeployed filtering device 20 is about 100 to about 400 microns, the inner diameter of hollow needle 102 may be in the range of about 100 to about 900 microns, and the outer diameter of hollow needle 102 may be in the range of about 200 to about 1000 microns. More specifically, the inner diameter of hollow needle 102 may be in the range of about 200 to about 400 microns, and the outer diameter of needle 102 may be in the range of about 300 to about 600 microns. Thus, the punctures made by hollow needle 102 in a patient's tissue may be sufficiently small (about 100 to about 900 microns) as to be self-sealing.

Hollow needle 102 may be made from any suitable biocompatible material, such as s, for example, stainless steel. Pusher 103 may also be made from a metal such as stainless steel. Handles 106 and 108 may be made from plastic.

In the absence of external load, filtering device 20, in some embodiments, assumes the deployed shape of FIG. 2B. To transform device 20 to an undeployed state, it may be stretched by applying axial force at both its ends using a special jig (not shown). The stretched device may then be inserted into the lumen of needle 102 by sliding the needle over the stretched, undeployed device. Twisting device 20 before or during insertion into needle 102 is also possible.

Figure 10B:
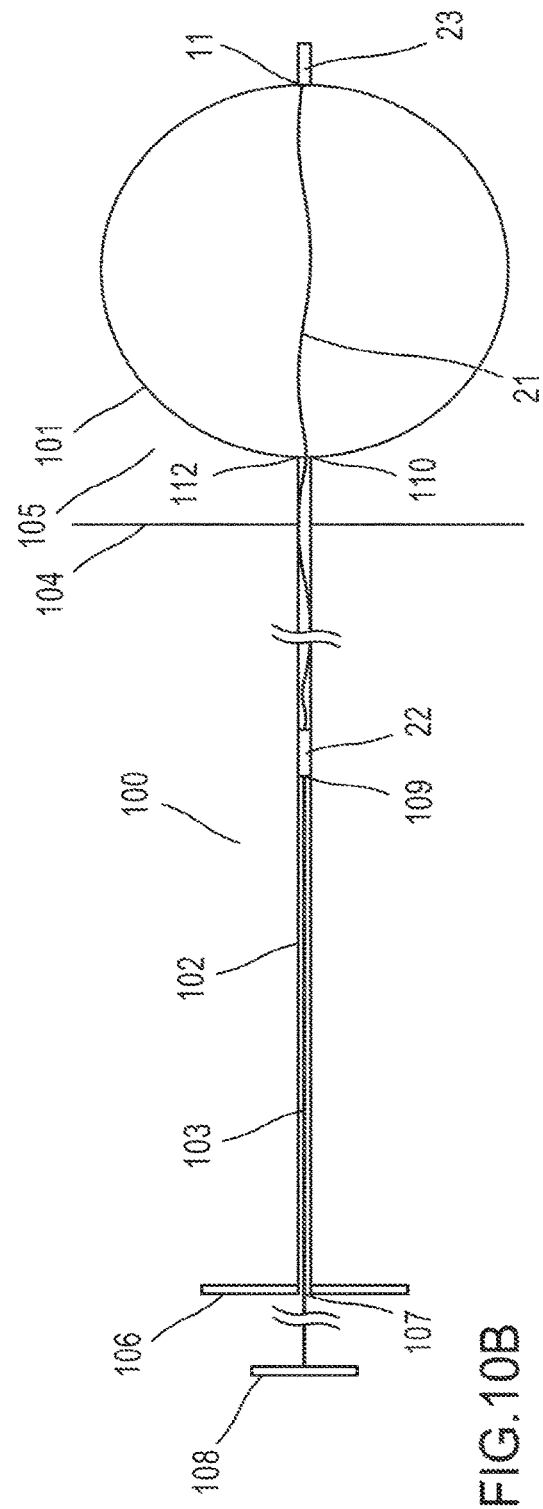
Figure 10E:
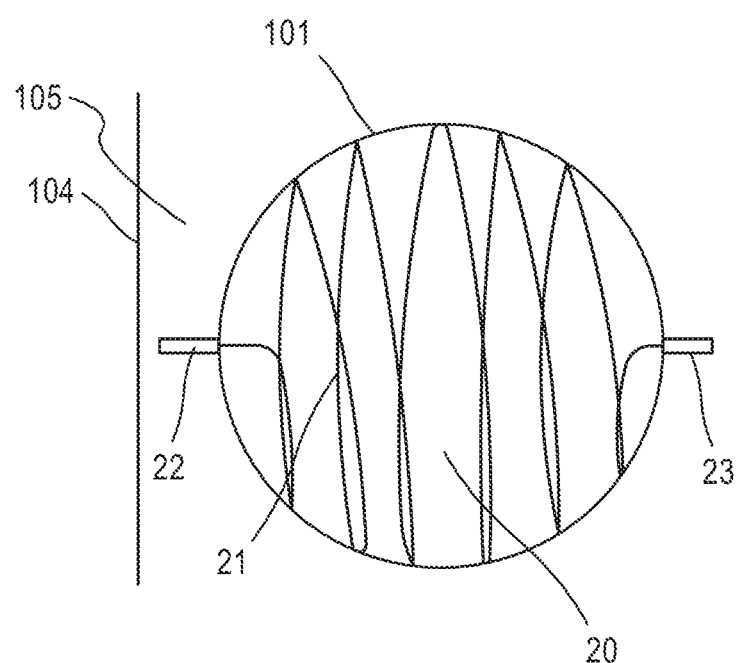

Both filtering device 20 and pusher 103 may be slidable within the lumen of hollow needle 102. Prior to deployment, filtering device 20 is located inside the lumen of needle 102 near its distal end 112. The distal end 109 of pusher 103 is also located inside the lumen of hollow needle 102. The distal end 109 of pusher 103 is in contact with the proximal end of end piece 22 of device 20. After deployment, as depicted in FIG. 10E, filtering device 20 may be exteriorized from hollow needle 102, and the distal end 109 of pusher 103 roughly coincides with distal end 112 of hollow needle 102.

The implantation of filtering device 20 in body vessel 101 may proceed as follows. First, a physician determines that it is desirable to implant filtering device 20 in body vessel 101. Under the guidance of a suitable imaging modality (not shown), such as, for example, ultrasound, high resolution ultrasound, CT scanning, or without imaging guidance at all, the operator punctures skin 104 adjacent to vessel 101 using the sharp end 112 of needle 102. Note that system 100 is in the configuration depicted in FIG. 10A, that is, with filtering device 20 housed in its undeployed state near the distal end of hollow needle 102. The operator then carefully advances delivery device 100 through the subcutaneous tissue, and transversely punctures vessel 101 at approximately diametrically-opposed sites 110 and 111. The first puncture 110 of vessel 101 is made on its side closer to skin 104 (proximal side), and the second puncture 111 is made on the diametrically-opposite side (distal side). The sharp end 112 of needle 102 may then be advanced a few more millimeters interiorly into the patient, so that end piece 23 may be exterior to the lumen of vessel 101. This situation is depicted in FIG. 10A.

Next, the operator holds pusher 103 substantially motionless while retracting hollow needle 102 backwards, away from the patient. This can be done with the aid of handles 106 and 108. In this way, end piece 23 of device 20 is exteriorized from needle 102. It then assumes its deployed state in the tissue proximate second puncture 111, thereby anchoring the distal end 23 of device 20 in the tissue. The needle may then be retracted until its distal end 112 roughly coincides with proximal puncture 110. This situation is depicted in FIG. 10B.

To exteriorize the remainder of device 20 from hollow needle 102, the operator advances pusher 103 towards the distal end 112 of needle 102 while holding the needle still. As device 20 is exteriorized from the needle, it gradually assumes its deployed, spring-like shape. This situation is depicted in FIG. 10C.

In some embodiments, exteriorizing device 20 may create torque along the principal axis of end-piece 23. In such embodiments, it may be advantageous for end piece 23 to comprise a hearing 34, thereby enabling the strain (torsion) pre-existing in filament 21 to release. This may also prevent torsion from building up during the exteriorization process. In such embodiments, the distal end of filament 21 rotates with end piece 23 as a pivot point while device 20 is exteriorized. The operator stops pushing the pusher once filament 21 is essentially exteriorized from needle 102 into the lumen of vessel 101, and end piece 22 is situated, still inside the lumen of needle 102, proximate its implantation site. The situation is then as depicted in FIG. 10D.

In some embodiments, to complete the implantation procedure, the operator holds pusher 103 steady while retracting needle 102 over the pusher. This causes the end piece 22 to be exteriorized at its implantation site and assume its deployed shape. Once the entire device 20 is exteriorized and implanted in its deployed state, both needle 102 and pusher 103 are exteriorized from the patient's body. This completes the implantation procedure for some embodiments, as depicted in FIG. 10E. Note that for some embodiments, because both the filtering device 20 and hollow needle 102 are of a sufficiently small diameter, all of the holes and the punctures made in body tissues during the procedure may be self-sealing. Therefore, the suturing or sealing of holes and punctures thus made is unnecessary. If it is determined that one or more additional filtering devices should be implanted in one or more additional implantation sites the procedure may be performed again, essentially as described above.

Implantation systems comprising devices 10, 60, 70, 74, and 80 are obtainable by exchanging device 20 in system 100 for any of these devices. The implantation methods corresponding to these systems thus obtained are substantially similar to the method corresponding to system 100. Therefore, the detailed description of these systems and methods is omitted.

Reference is now made to FIGS. 11A-11D, which illustrate a method for providing embolic protection and a system for delivering an embolic protection device according to some embodiments of the present disclosure. The system and method are particularly suitable for delivering a filtering device 24 comprising one end piece 22 at its proximal end. A single proximal puncture of the target vessel is required, as opposed to two diametrically opposed punctures as in the method corresponding to system 100.

FIG. 11A depicts a system 113 configured to implant a filtering device 24 in a body vessel 101. System 113 is substantially similar to system 100, except that filtering device 20 is exchanged for filtering device 24.

In some embodiments, the implantation of filtering device 24 in body vessel 101 may proceed as follows. First, a physician determines that it is desirable to implant filtering device 24 in body vessel 101. Under the guidance of a suitable imaging modality (not shown), such as, for example, ultrasound, high resolution ultrasound, or CT scanning, or without imaging guidance at all, the operator punctures skin 104 adjacent to vessel 101 using the sharp end 112 of needle 102. The operator then carefully advances system 113 through the subcutaneous tissue, and punctures vessel 101 using the sharp end 112, of needle 102. The orientation of the needle is roughly perpendicular to the wall of vessel 101 at the point of contact (puncture 110) of the needle and the vessel wall. The operator then slightly advances system 113 such that sharp end 112 of needle 102 slightly protrudes into the lumen of vessel 101. This situation is depicted in FIG. 11A.

Next, the operator exteriorizes filament 21 of device from needle 102 by holding needle 102 in place and advancing pusher 103. As filament 21 is exteriorized front the needle, its exteriorized portion assumes its deployed shape in the lumen of vessel 101. The distal tip 11 of device 24 approximately traces the deployed helical shape of device 24 as filament 21 is exteriorized. This situation is depicted in FIG. 11B.

As proximal turn 16 of device 24 is exteriorized from needle 102, the primary axis (that is, roughly the line segment connecting distal tip 11 and end piece 22) becomes collinear with needle 102. As a result, the primary axis of device 24 ends up approximately perpendicular to the fluid flow in vessel 101, and approximately bisects a perpendicular cross section of vessel 101. This situation is depicted in FIG. 11C.

In some embodiments, to complete the implantation procedure the operator holds pusher 103 steady while retracting needle 102 over the pusher. This causes end piece 22 to be exteriorized at its implantation site proximal puncture 110 and assume its deployed shape. Once the entire device 24 is exteriorized and implanted in its deployed state, both needle 102 and pusher 103 are exteriorized from the patient's body. This completes the implantation procedure, as depicted in FIG. 11D. Note that in some embodiments, because both the filtering device 24 and hollow needle 102 are of a sufficiently small diameter, all of the holes and the punctures made in body tissues during the procedure may be self-sealing. Therefore, the suturing or sealing of holes and punctures thus made is unnecessary. If it is determined that one or more additional filtering devices should be implanted in one or more additional implantation sites the procedure may be performed again, essentially as described above.

We note that in embodiments according to the present disclosure in which distal tip 11 is sharp, it is possible to puncture the wall of vessel 10i using tip 11 instead of sharp end 112 of needle 102. In fact, in all of the embodiments of filtering devices according to the present disclosure in which the distal tip of the device is sharp, it is possible to create one or more punctures in the vessel wall using tip 11 instead of the sharp end of needle 102.

Implantation systems comprising devices 17, 62, and 72 are obtainable by exchanging device 24 in system 113 for any of these devices. The implantation methods corresponding to the systems thus obtained are substantially similar to the method corresponding to system 113. Therefore, a detailed description of these systems and methods is omitted.

In some embodiments, delivery devices in which needle 102 has a variable diameter are provided.

In some embodiments, the implantation of a filtering device according to the present disclosure results in the distal end of the device apposing the vessel wall at a location roughly diametrically opposed to the puncture she. The distal end (or distal end-piece, where applicable) may partially or completely penetrate the vessel wall. The proximal end (or proximal end-piece, where applicable) may be located outside the lumen of the vessel, across the will of the vessel, or inside the lumen of the vessel. Any wall penetration depth (none, partial, complete) is possible in the deployed state of embolic protection devices according to the present disclosure.

Figure 12A:
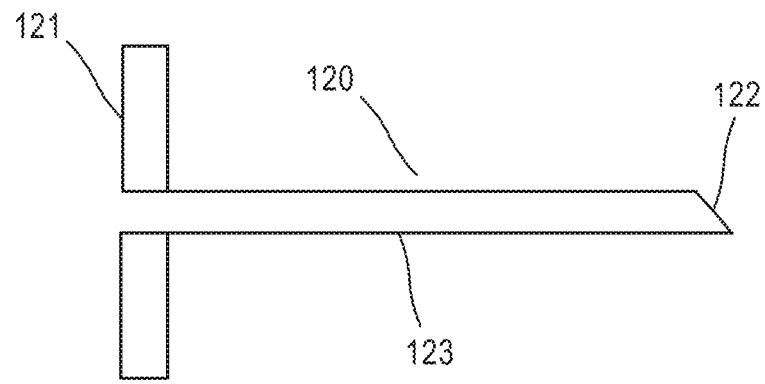
FIGS. 12A and 12B depict the components of an apparatus for retrieving a filtering device according to some embodiments of the present disclosure.
Figure 12B:
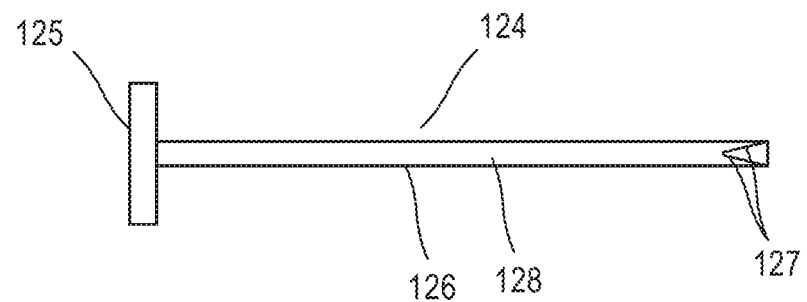

Reference is now made to FIGS. 12A and 12B, which depict components of a retrieval apparatus according to some embodiments according to the present disclosure. The retrieval apparatus is particularly suitable for minimally-invasive explantation and retrieval of embolic, protection devices according to some embodiments, which comprise a proximal end-piece having a retrieval knob.

FIG. 12A depicts extraction sheath 120, which comprises a hollow sheath 123 having a lumen and a sharp end 122, and a handle 121. The internal diameter of hollow sheath 123 is configured to be larger than the diameter of retrieval knob 37 of proximal end-piece of device 60. (We note that device 60 was chosen by way of example: any embodiment of a filtering device according to the present disclosure and comprising a retrieval knob may be retrieved using the retrieval apparatus of FIGS. 12A and 12B.)

FIG. 12B depicts a grasper 124, which comprises hollow sheath 126 and handle 125. The distal end of sheath 126 comprises springy, flexible leaflets 127, which may bend towards the inner walls of lumen 128 of sheath 126, yet are limited by each other in bending towards the center of lumen 128.

Figure 13A:
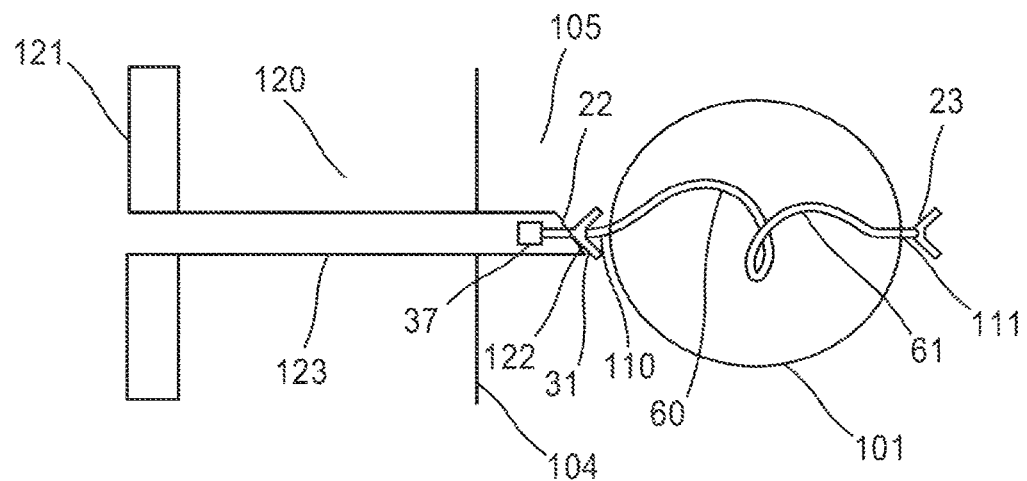

Reference is now made to FIGS. 13A-13F, which depict some methods of retrieval according the some embodiments of the present disclosure. First, it is determined by the operator that is desirable to retrieve, for example, an embolic protection device 60, which comprises a proximal end-piece having a retrieval knob 37, from its implantation site in a body vessel. Then, using a suitable imaging modality such as ultrasound, high resolution ultrasound, CT, or MRI, the operator punctures the patient's skin 104 using extraction sheath 120, and advances the distal tip 122 of hollow sheath 123 over knob 37 of proximal end-piece 22. This situation is depicted in FIG. 13A. Note that distal tip 122 may reside either externally to the vessel, as depicted in FIG. 13A, in the vessel wall, or in the lumen.

Figure 13B:
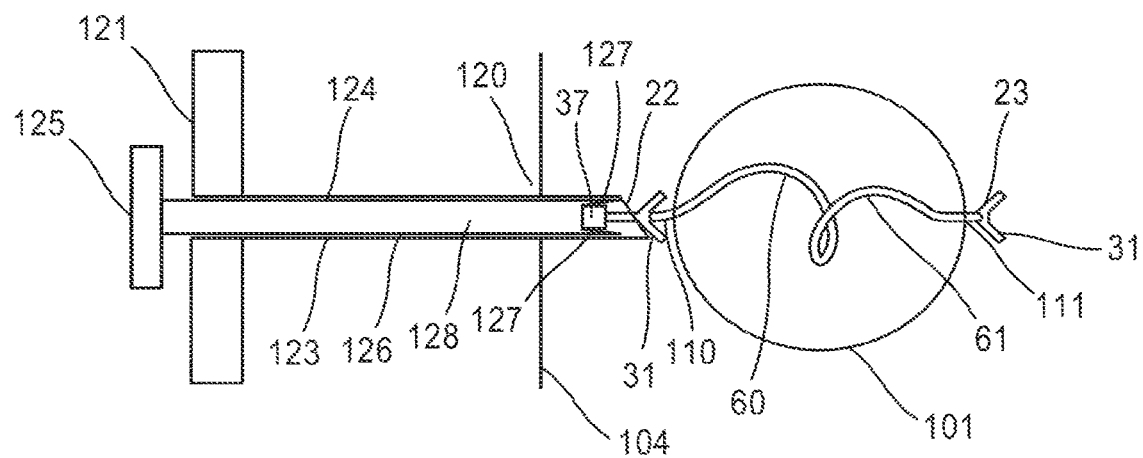
Figure 13E:
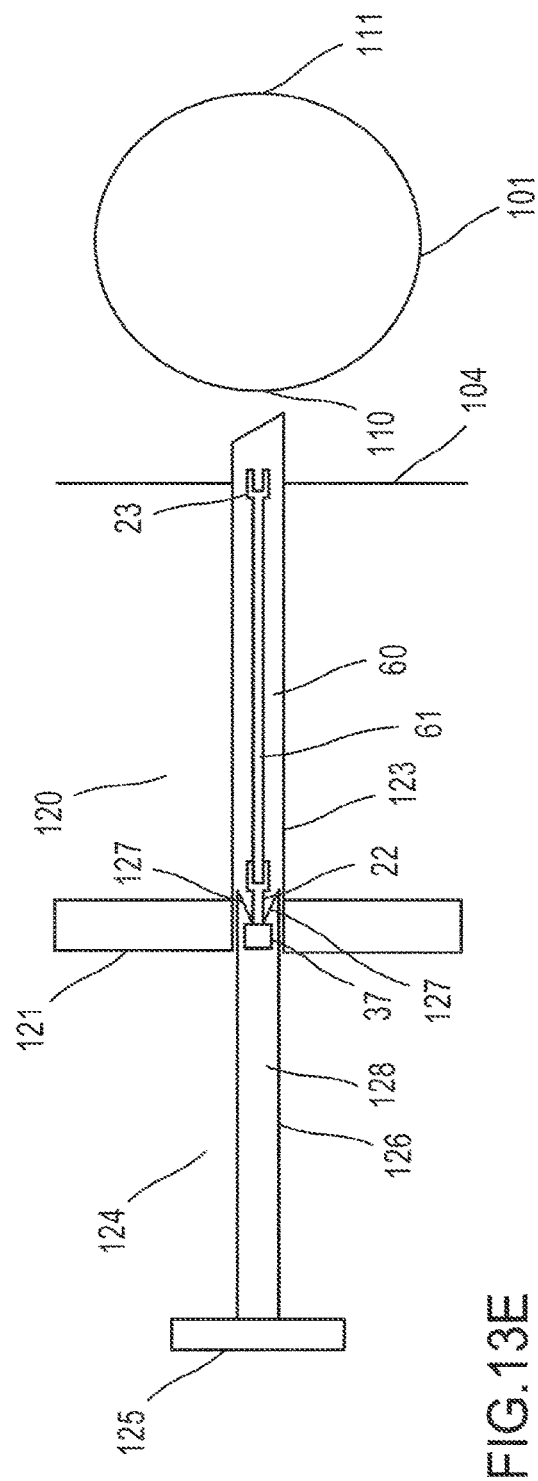
Figure 13F:
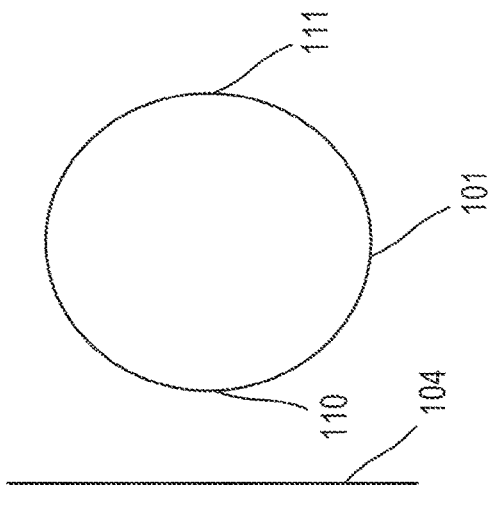

Next the operator advances grasper 124 inside the lumen of hollow sheath 123, while hollow sheath 123 is maintained in place. The distal end of sheath 126 then touches knob 37 of end-piece 22. Flexible springy leaflets 127 are then pushed outwards towards the walls of lumen 128 by knob 37. This situation is depicted in FIG. 13B.

The operator then continues to push grasper 124 while holding extraction sheath 120 in place. The proximal ends of springy leaflets 127 then extend distally to the distal end of knob 37. The knob is now inside lumen 128 of sheath 126. Due to the "ratchet" effect between the leaflets and the knob, grasper 124 can no longer be retracted over knob 37. It is irreversibly attached to knob 37. This situation is depicted in FIG. 13C.

Next, the operator maintains extraction sheath 120 in place while retracting grasper 124. Flexible leaflets 127 thus pull on knob 37, thereby forcing end piece 22 into its undeployed state, straightening device 60, and retracting it into the lumen of hollow sheath 123. This situation is depicted in FIG. 13D. Further retraction of grasper 124 brings about the situation depicted in FIG. 13E: The pulling force generated by retracting grasper 124 is transmitted through straightened filament 61 thereby causing end piece 23 to assume its undeployed shape and ultimately to retract into the lumen of hollow sheath 123.

Finally, extraction sheath 120, extractor 124, and device 60 are jointly retracted by the operator from the patient's body. The small punctures 110 and 111 in vessel 101 self-seal. The retrieval procedure is over.

It will be noted that an apparatus for retracting retrievable embodiments of devices 20, 24, 62, 72, 74, and 80, and their corresponding retrieval methods, are substantially similar to the retrieval apparatus and method described for device 60. A detailed description will therefore be omitted.

Figure 14A:
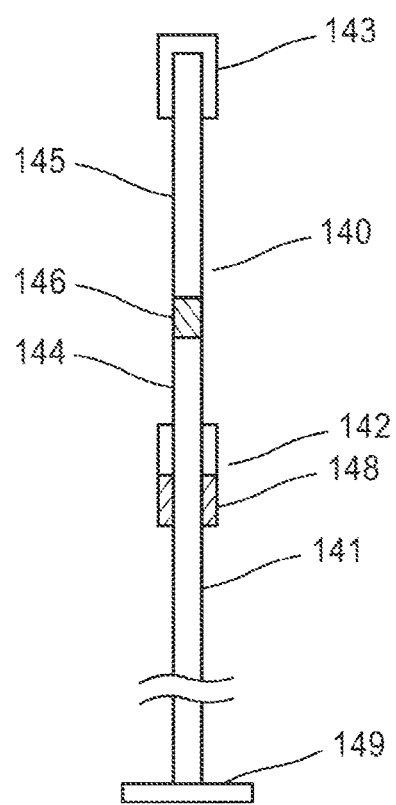
FIGS. 14A and 14B respectively depict undeployed and deployed states of a vessel occlusion device according to some embodiments of the present disclosure.
Figure 14B:
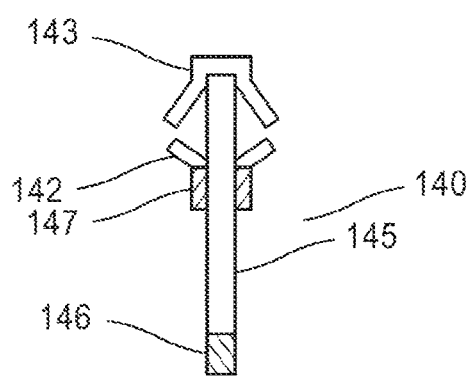

Reference is now made to FIGS. 14A and 14B, which depict undeployed and deployed states, respectively, of a body-vessel occlusion device according to some embodiments of the present disclosure. An occlusion device of this type provides embolic protection by completely occluding the target vessel in which it is implanted. It may be particularly useful, for example, in preventing the embolization of sclerosant utilized in a saphenous vein in the course of varicose vein treatment.

Occlusion device 140 of FIG. 14A may comprise a filament 141, a proximal anchor 142, and a distal anchor 143. Filament 141 may be separated into a proximal part 144 and a distal part 145 at separation point 146. The proximal and distal parts 144 and 145 are initially-connected at separation point 146, and may be disconnected upon the application of external force or signal. A removable handle 149 may optionally be attached to proximal part 144 at its proximal end.

The initial connection between parts 144 and 145 may be mechanical. For example, part 144 may screw into part 145, and disconnection of the parts may be brought about by unscrewing them. Alternatively, filament 141 may comprise a conducting core cladded with an insulating layer at every point along its length except for separation point 146. When it is desired to separate parts 144 and 145, electrical current from an external source (not shown) is run through filament 141, thereby causing electrolysis and subsequent disconnection of parts 144 and 145 at separation point 146.

Proximal anchor 142 may be slidable over filament 141. For example, proximal anchor 142 may comprise a slidable element 14l configured to slide over filament 141. Slidable element 148 may comprise a locking mechanism that fixes it in a desired location along filament 141.

In its undeployed state, occlusion device 140 may be configured to reside in the lumen of a fine needle, substantially collinear with the lumen of the needle. The anchors 143 and 142 assume their undeployed configuration when device 140 is in its undeployed state.

The undeployed length of occlusion device 140 may be in the range of several centimeters to about 100 cm. The diameter of occlusion device 140 may preferably be less than about 1.0 mm. In particular, the diameter of occlusion device 140 may preferably be less than about 0.5 mum, and even more particularly, less than about 0.2 mm.

Separation point 146 may be between about 1 mm and about 30 m from the distal end of occlusion device 140.

In the deployed state of occlusion device 140 (FIG. 14B), anchors 142 and 143 may be in their deployed configuration. Anchor 142 may be moved towards anchor 143 such that the distance between them is typically between about 1 mm and about 10 mm. The most proximal point of anchor 142 is distal to separation point 146. Proximal part 144 of filament 141 is separated from distal part 145. Thus, the deployed state of occlusion device 140 comprises distal part 145 of filament 141 and no longer comprises the proximal part 144.

Occlusion device 140 may be configured to be relatively stiff or, in some embodiments, relatively flexible. Alternatively, occlusion device 140 may be configured to assume any degree of flexibility. Stiffness and diameter along the length of filament 140 may be variable.

Occlusion device 140, according to some embodiments of the present disclosure, may be configured as a solid filament. Alternatively, it may be configured as a tube having a hollow lumen, or as a tube having its ends closed-off, thereby leaving an elongated air-space inside occlusion device 140. Leaving an air-space inside occlusion device 140 may have the advantage of making occlusion device 140 more echogenic and therefore more highly visible by ultrasound imaging. Occlusion device 140 may possess an echogenic marker or a radiopaque marker.

Occlusion device 140 may be made, for example, from any of the materials that devices 10 or 20 may be made of, as described earlier in this document.

Figure 15A:
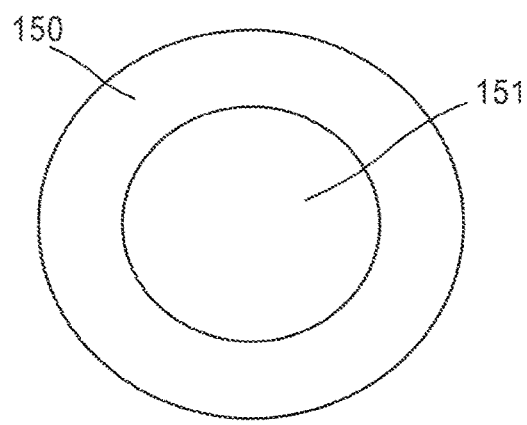
FIGS. 15A and 15B respectively depict a perpendicular cross section of a body vessel before and after the implantation of the occlusion device of FIGS. 14A and 14B.
Figure 15B:
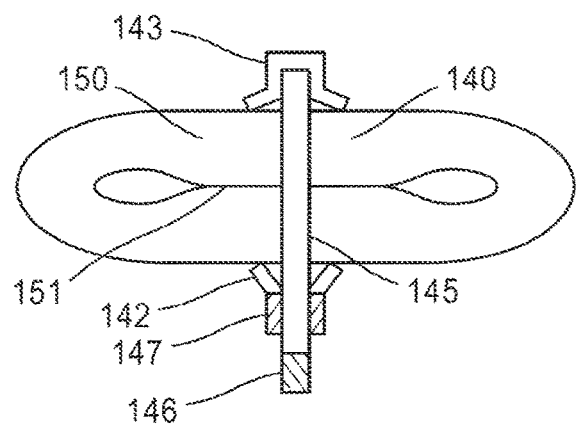

Reference is now made to FIG. 15A, which depicts a schematic cross-sectional view of a blood vessel before implantation of occlusion device 140. Reference is also made to FIG. 15B, which depicts a schematic cross-sectional view of the blood vessel after implantation of device 140.

FIG. 15A shows the circular cross-section of a patent blood vessel 150, such as an artery or a vein, in which blood is free to flow in vessel lumen 151. Suitable veins may be, for example, perforators of the great saphenous vein. Upon implantation of occlusion device 140 in blood vessel 150 (FIG. SB), anchors 143 and 142, which are brought close together, push against opposite sides of the vessel wall, thereby flattening a perpendicular cross section of the vessel. As a result, lumen 151 disappears, or substantially disappears. Thus, occlusion device 140 causes vessel 150 to become either totally or substantially occluded.

Figure 16A:
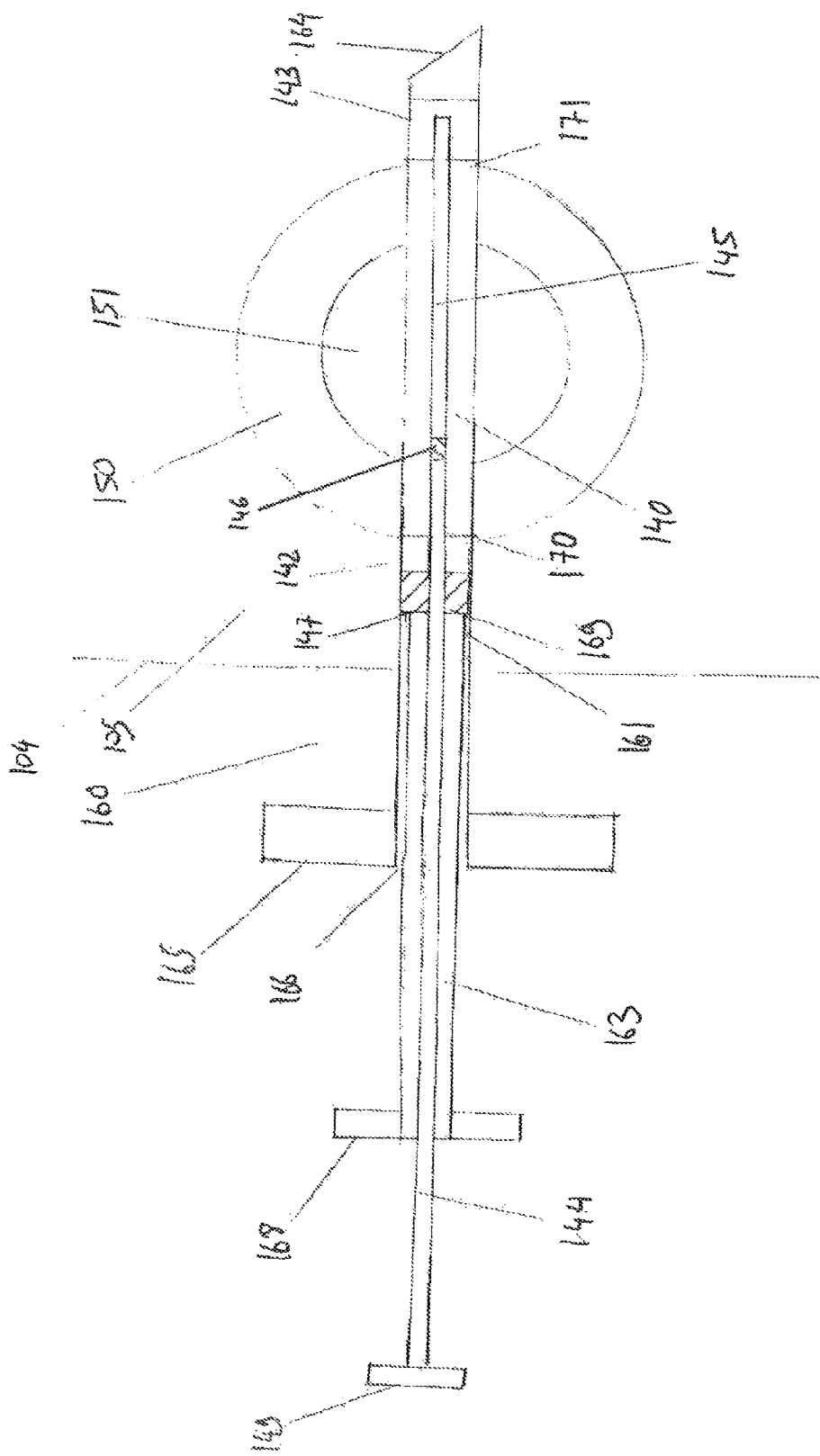
FIGS. 16A-16E depict a system and method according to some embodiments of the present disclosure, which are intended for implanting an occlusion device according to some embodiments of the present disclosure.

Reference is now made to FIGS. 16A-16E, which depict a method for vessel occlusion and an apparatus for implanting a (partial or total) occlusion device according to some embodiments of the present disclosure. FIG. 16A depicts a delivery device 160 configured to implant occlusion device 140 in body vessel 150. Delivery device 160 comprises a hollow needle 161, push tube 163, and occlusion device 140. Hollow needle 161 has a sharp end 164 configured to pierce skin 104, subcutaneous tissue 105, and body vessel 150 of a patient. Needle 161 may have a needle handle 165 located at its proximal end 166. The needle handle 165 may be rigidly connected to needle 161. Push tube 163 may have a push tube handle 168. The push tube handle 168 may be rigidly connected to push tube 163.

Hollow needle 161 may have a very small inner and outer diameter. For example, if the maximal collapsed diameter of undeployed occlusion device 140 is 200 microns, the inner diameter of hollow needle 161 may be in the range of 200-600 microns, and the outer diameter of hollow needle 161 may be in the range of 300-800 microns. Thus, the punctures made by hollow needle 161 in a patient's tissue may be sufficiently small (100-900 microns) as to be self-sealing.

Hollow needle 161 may be made from any suitable biocompatible material, such as, for example, stainless steel. Push tube 163 may also be made from a metal such as stainless steel. Handles 165 and 168 may be made from plastic.

Occlusion device 140 and push tube 163 may both be slidable within the lumen of hollow needle 161. Occlusion device 140 may also be slidable within the lumen of push tube 163.

Prior to deployment, occlusion device 140 may be slidably received inside the lumen of push tube 163. In some embodiments, the distal end 169 of push tube 163 is in contact with the proximal end of slidable element 147 of anchor 142. Both occlusion device 140 and push tube 163 are slidably received in the lumen of needle 161. The distal anchor 143 of occlusion device 140 is located near the sharp end 164 of needle 161.

In some embodiments, the implantation of occlusion device 140 in body vessel 150 may proceed as follows: First, an operator determines that it is desirable to implant occlusion device 140 in body vessel 150. Under the guidance of a suitable imaging modality (not shown), such as, for example, ultrasound, high resolution ultrasound, or CT scanning, or without imaging guidance at all, the operator punctures skin 104 adjacent to vessel 150 using the sharp end 164 of needle 161. Note that delivery device 160 is in the configuration depicted in FIG. 16A, that is, with the distal end of occlusion device 140 near the distal end of hollow needle 161, and in its undeployed, substantially-linear, substantially-straight wire state. The operator then carefully advances delivery device 160 through the subcutaneous tissue 105, end transversely punctures vessel 140 at approximately diametrically-opposed sites 170 and 171. The first puncture 170 of vessel 150 is made on its side closer to skin 104, and the second puncture 171 is made on the diametrically-opposite side. Note that the second puncture 171 may be either complete or partial: Sharp end 164 of needle 161 may completely traverse the wall of vessel 150, or alternatively, only breach the inside (lumen side), but not the outside of the wall. The sharp end 164 of needle 161 may then be advanced a few more millimeters interiorly into the patient. This situation is depicted in FIG. 16A.

Figure 16B:
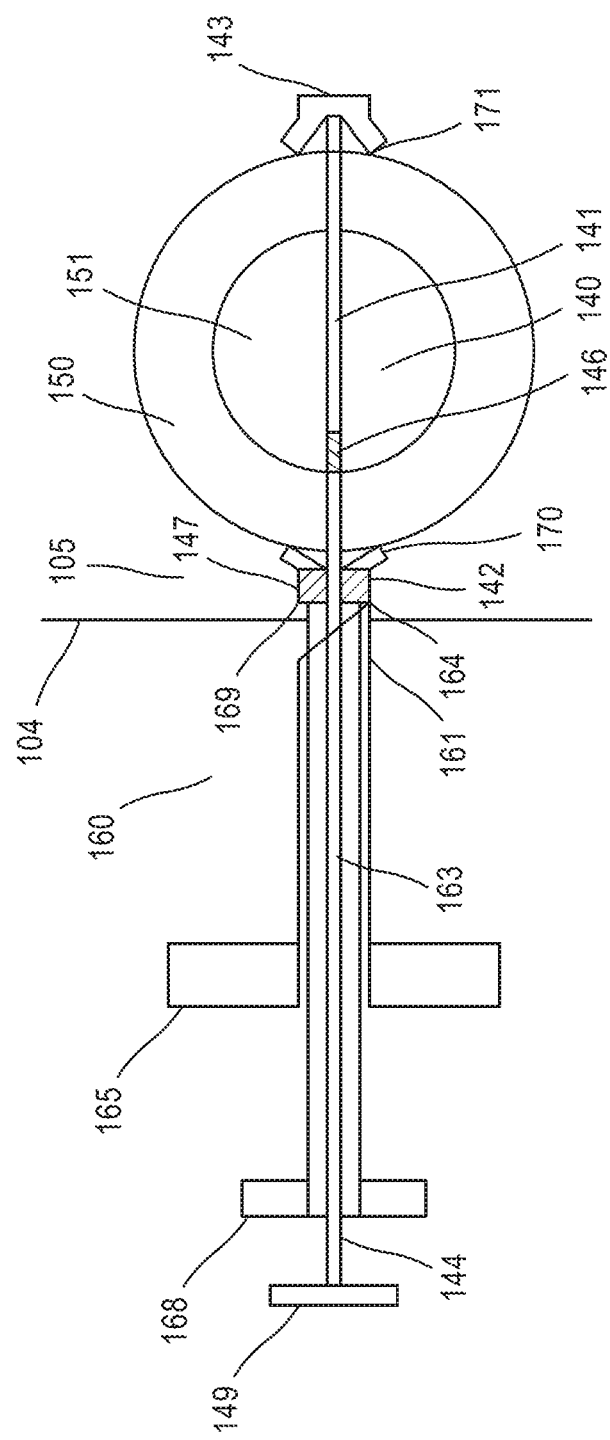

Next, by means of handles 165, 149 and 168, the operator holds occlusion device 140 and push tube 163 substantially motionless while retracting hollow needle 161 backwards, away from the patient. Thus, the distal end 164 of hollow needle 161 is retracted over occlusion device 140 and push tube 163 until both anchors 142 and 143 are exteriorized from needle 161. Anchor 143 is exteriorized distally to the lumen 151, and anchor 142 is exteriorized proximally to the lumen 151. Each anchor assumes its deployed state following exteriorization. This situation is depicted in FIG. 16B.

It is noted that all absolute and relative motions of device 140, needle 161 and push tube 163, may be made using an automated mechanism, such as, for example, an automated electro-mechanical mechanism (not shown).

Figure 16C:
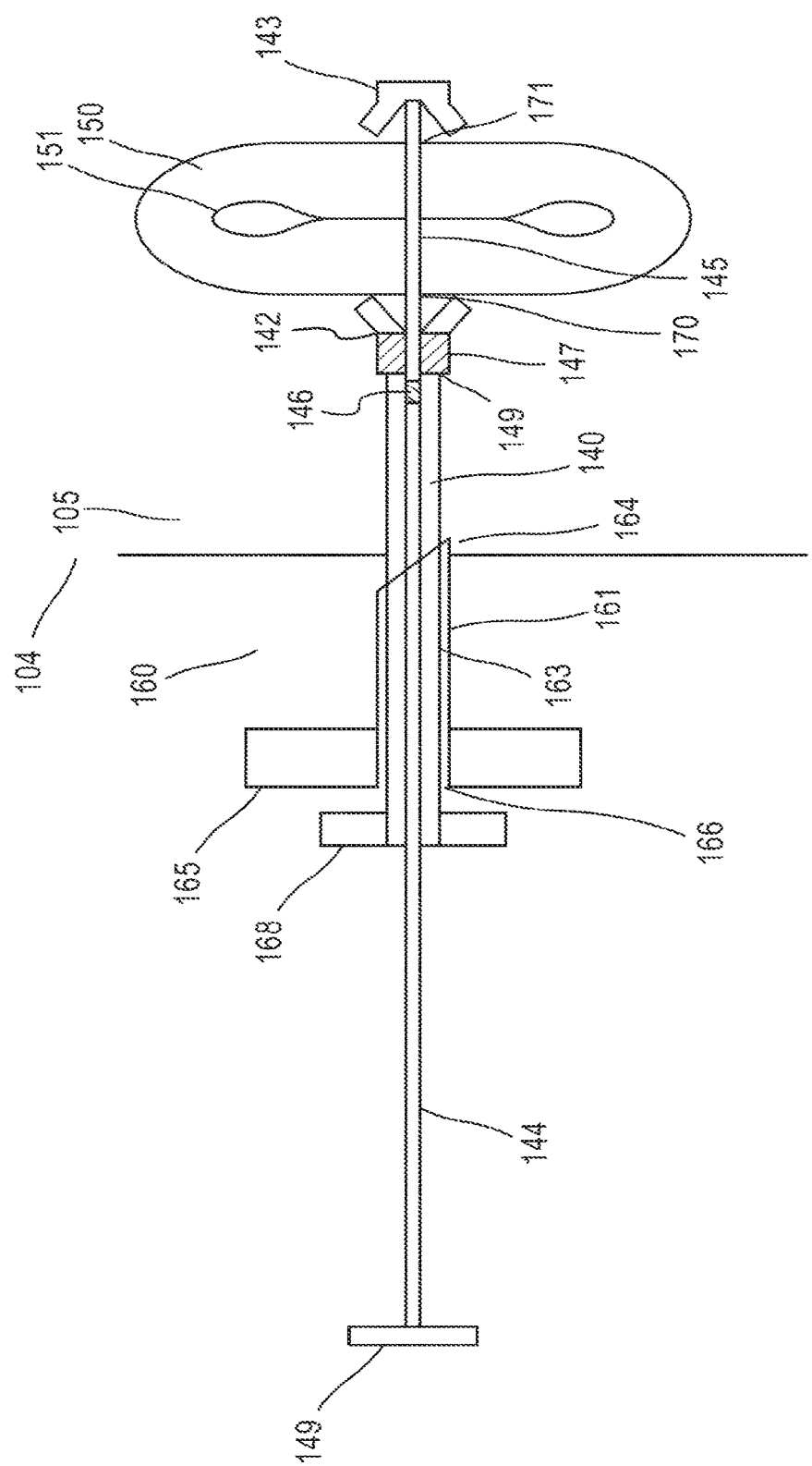
Figure 16D:
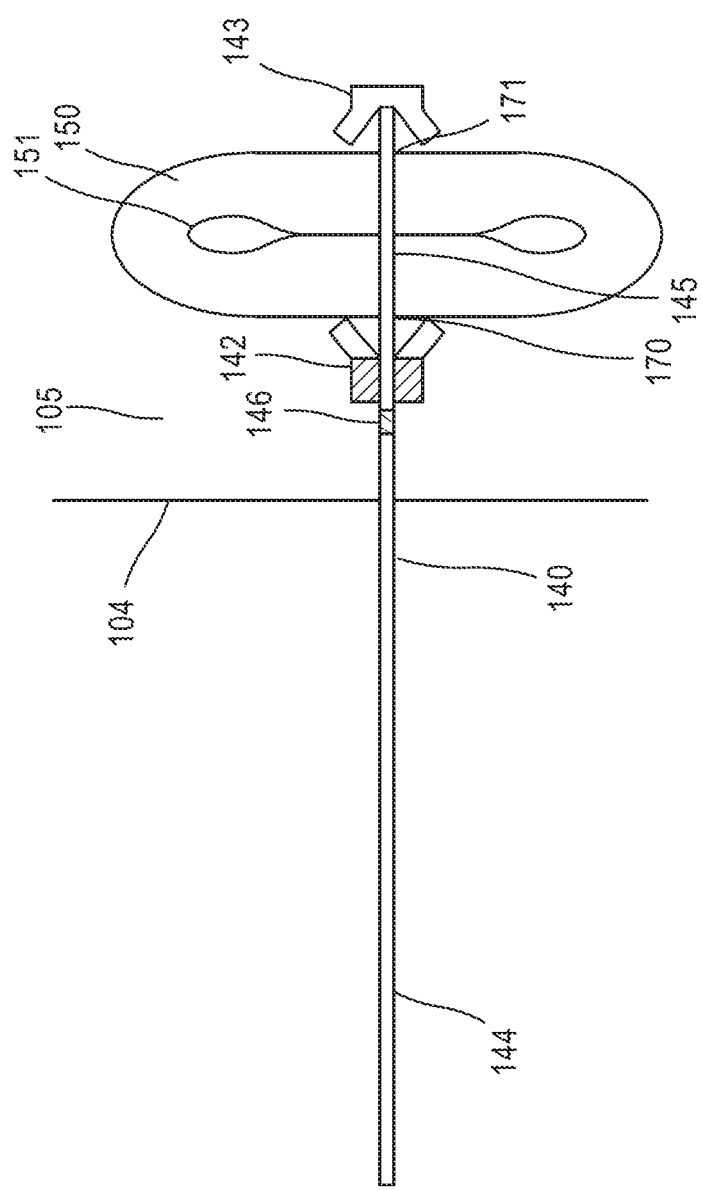
Figure 16E:
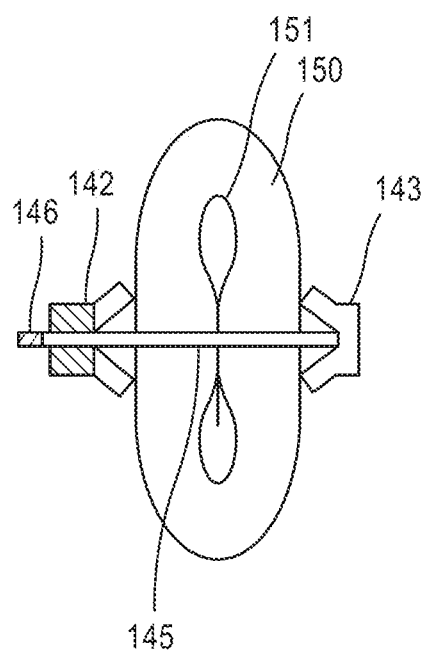

In the next step, by means of handles 165, 149, and 168, the operator holds occlusion device 140 and needle 161 substantially motionless while advancing push tube 163 towards distal anchor 143. Push tube 163 thus pushes proximal anchor 142, causing it to slide towards distal anchor 143. The operator continues to advance push tube 163 until proximal anchor 143 slides past separation point 146 and the distance between anchors 142 and 143 is sufficiently small as to flatten vessel 150 and annul its lumen 151, either totally or partially, as desired. Slidable anchor 142 is then locked in place and cannot slide proximally. This situation is depicted in FIG. 16C.

Next, the operator removes removable handle 149 from proximal part 144 of occlusion device 140. The operator then exteriorizes from the patient's body both needle 161 and push tube 163 over both distal part 145 and proximal part 144 of device 140. The situation is depicted in FIG. 16B.

In the next step, the operator disconnects proximal part 144 of device 140 from the remainder of the device. Disconnection may be brought about by, for example, unscrewing part 144 from part 145. If, for example, filament 144 of device 140 has an electricity-conducting core and an insulating cladding everywhere except separation point 146, the operator may separate parts 144 and 145 by running a sufficiently high electric current in the filament. Finally, the operator exteriorizes part 144 from the patient's body, which completes the implantation procedure (FIG. 6E).

It is understood that monofilament filtering devices according to some embodiments of the present disclosure are possible in which, in a deployed state, the proximal end of the monofilament extends exteriorly from the patient's skin, or is implanted subcutaneously immediately below the patient's skin. Such devices are particularly suited for temporary usage, in which it is desired to retrieve the device shortly after a temporary embolus-enticing cause, such as surgery or minimally-invasive procedure, is removed.

In order to prevent stroke, filtering devices according to some embodiments of the present disclosure may be implanted in an artery supplying blood to the brain, such an aorta, a common carotid artery, an internal carotid artery, a subclavian artery, a brachiocephalic artery, or a vertebral artery.

In order to prevent pulmonary embolism, filtering devices according to some embodiments of the present disclosure may be implanted in a vein such as a superficial femoral vein, a deep femoral vein, a popliteal vein, an iliac vein, an inferior vena cava, or a superior vena cava.

Implantation systems of some embodiments of the embolic protection devices described herein are possible, which are automatic and/or electro mechanical.

The pusher in implantation systems according to the present disclosure need not be solid: exteriorization of embolic protection devices according to the present disclosure using pressurized fluid, liquid, or gas is possible.

Although a few variations of the embodiments have been described in detail above, other modifications to such embodiments are possible, enabling still other embodiments. For example, any logic flow depicted in the accompanying figures and/or described herein does not require the particular order shown, or sequential order, to achieve desirable results. Other implementations may be within the scope of at least some of the following exemplary claims.

Accordingly, exemplary embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims which may be supported by the present disclosure and their equivalents. Moreover, embodiments of the subject disclosure may include methods, systems and devices which may further include any and all elements from any other disclosed methods, systems, and devices, including any and all elements. In other words, elements from one or another disclosed embodiment may be interchangeable with elements from other disclosed embodiments, thereby supporting yet other embodiments. In addition, one or more features/elements of disclosed embodiments may be removed and still result in patentable subject matter (and thus, resulting in yet more embodiments of the subject disclosure).

What is claimed is:

1. An embolic protection device configured for implantation into a body vessel comprising:
    a filament including an undeployed state configured for delivery via a lumen of a tube, and a deployed state configured to assume a shape of a helix having a plurality of windings or turns;
    and
    an end-piece having at least one prong formed from a shape memory or super-elastic material,
    wherein:
    an end of the filament is received within and connected to the end piece, and
    upon transition of the filament from the undeployed state to the deployed state, the at least one prong of the end piece extends outwards from the end-piece to anchor the end of the filament in tissue.

2. The device of claim 1, wherein the windings or turns vary in diameter.

3. The device of claim 1, wherein at least one of the tube and a distal end of the filament is configured for puncturing the vessel.

4. The device of claim 1, wherein the filament includes a substantially circular cross-section.

5. The device of claim 1, wherein the thickness of the filament is between about 50 and 500 microns.

6. The device of claim 1, wherein in the deployed state, the radius of curvature anywhere along the filament exceeds a critical value equal to the thickness of the filament divided by about twice the critical strain of the material from which the filament is made.

7. The device of claim 6, wherein the critical value is greater than about 0.6 mm.

8. The device of claim 1, wherein the helix includes between one and twenty turns.

9. The device of claim 1, wherein the helix comprises a plurality of turns and wherein the distance between consecutive turns is greater than about 0.7 mm.

10. The device of claim 1, wherein the helix comprises a plurality of turns and wherein the distance between consecutive helix turns is less than about 1.5 mm.

11. The device of claim 1, further comprising one or more of a radiopaque marker, an echogenic marker, a radioactive marker, a magnetic marker, and a magnetic resonance marker.

12. The device of claim 1, wherein:
    the end piece includes a plurality of prongs, and/or
    the end-piece comprises a separate end-piece from the filament.

13. The device of claim 1, further comprising one or more additional filaments.

14. The device of claim 13, wherein said one or more additional filaments each have a helical shape.

15. The device of claim 1, wherein the at least one prong comprises at least a pair of prongs, the at least a pair of prongs comprising a first prong and a second prong.

16. The device of claim 15, wherein in the undeployed state, each of the first and second prongs of the at least a pair of prongs is aligned with, positioned adjacent, or within the external surface of the end-piece.

17. The device of claim 1, wherein the first prong of the at least a pair of prongs is spaced apart from the second prong of the at least a pair of prongs approximately 180 degrees.

18. The device of claim 1, wherein in the undeployed state, the at least one prong is aligned with, positioned adjacent, or within the external surface of the end-piece.

19. The device of claim 1, wherein upon transition of the filament from the undeployed state to the deployed state, the filament includes a linear segment provided on an end of the filament which is configured after implantation to traverse the vessel wall perpendicular to the fluid flow of the vessel or approximately thereto.

20. An embolic protection device configured for implantation into a body vessel comprising:
    a filament including an undeployed state configured for delivery via a lumen of a tube, and a deployed state configured to assume a shape of a helix having a plurality of windings or turns;
    and
    an end-piece having at least one prong formed from a shape memory or super-elastic material,
    wherein:
    the end piece is connected to an end of the filament,
    the at least one prong is, in the undeployed state, positioned within a plane defined by an external surface of the end-piece.

21. The device of claim 20, wherein upon transition of the filament from the undeployed state to the deployed state, the at least one prong of the end piece extends outwards from the end-piece to anchor the end of the filament in tissue.

* * * * *